US012790721B2

(12) United States Patent
Sun

(10) Patent No.: US 12,790,721 B2
(45) Date of Patent: Nov. 10, 2026

(54) METHODS AND COMPOSITIONS FOR IDENTIFYING TRAITS USING A CELL-FREE SYSTEM

(71) Applicant: Synvitrobio, Inc., San Leandro, CA (US)

(72) Inventor: Zachary Z. Sun, San Leandro, CA (US)

(73) Assignee: SYNVITROBIO, INC., San Leandro, CA (US)

(*) Notice: Subject to any disclaimer, the term of this patent is extended or adjusted under 35 U.S.C. 154(b) by 1024 days.

(21) Appl. No.: 17/802,377

(22) PCT Filed: Mar. 1, 2021

(86) PCT No.: PCT/US2021/020293
§ 371 (c)(1),
(2) Date: Aug. 25, 2022

(87) PCT Pub. No.: WO2021/174199
PCT Pub. Date: Sep. 2, 2021

(65) Prior Publication Data
US 2023/0212555 A1 Jul. 6, 2023

Related U.S. Application Data

(60) Provisional application No. 62/983,007, filed on Feb. 28, 2020.

(51) Int. Cl.
*C40B 30/04* (2006.01)
*C12N 15/10* (2006.01)

(52) U.S. Cl.
CPC .......... *C40B 30/04* (2013.01); *C12N 15/1058* (2013.01); *C12N 15/1062* (2013.01)

(58) Field of Classification Search
None
See application file for complete search history.

(56) References Cited

U.S. PATENT DOCUMENTS 3,396,223 A 8/1968 Stark, Jr.
3,515,782 A 6/1970 Nolan
(Continued)

FOREIGN PATENT DOCUMENTS

EP 3040418 A1 7/2016
WO 02/089498 A2 11/2002
(Continued)

OTHER PUBLICATIONS

Buntru, 2014, Tobacco BY-2 cell-free lysate: an alternative and highly-productive plant-based in vitro translation system, BMC Biotechnology 14(1):37.
(Continued)

*Primary Examiner* — Christian C Boesen
(74) *Attorney, Agent, or Firm* — Brown Rudnick LLP; Adam M. Schoen

(57) ABSTRACT

Provided herein are methods and compositions for screening using an in vitro transcription/translation (TXTL) system. In some embodiments, a screening method can include: providing a library of genetic candidates to be screened, each genetic candidate encoding one or more protein of interest; expressing each genetic candidate in an in vitro transcription/translation (TXTL) system, thereby producing a plurality of compositions each comprising the one or more protein of interest; and subjecting the plurality of compositions to an assay for assessing a desired phenotype, thereby determining whether the one or more protein of interest exhibits the desired phenotype.

20 Claims, 5 Drawing Sheets

Specification includes a Sequence Listing.

(56) References Cited

U.S. PATENT DOCUMENTS

| | | | | |
|---|---|---|---|---|
| 2005/0260653 | A1* | 11/2005 | Labaer | G01N 33/543 435/6.12 |
| 2006/0053512 | A1 | 3/2006 | Bao et al. | |
| 2018/0237847 | A1 | 8/2018 | Culler et al. | |
| 2020/0048629 | A1 | 2/2020 | Greenleaf et al. | |

FOREIGN PATENT DOCUMENTS

| | | | |
|---|---|---|---|
| WO | 03/037302 | A1 | 5/2003 |
| WO | 2005/108615 | A2 | 11/2005 |
| WO | 2016/183029 | A1 | 11/2016 |
| WO | 2016/187466 | A1 | 11/2016 |
| WO | 2018/154021 | A1 | 8/2018 |
| WO | 2018/165159 | A1 | 9/2018 |

OTHER PUBLICATIONS

Chiao, 2016, Development of prokaryotic cell-free systems for synthetic biology, bioRxiv, p. 048710.

Craig, 2010, Optimizing nucleotide sequence ensembles for cominatorial protein libraries using a genetic algorithm, Nucleic Acids Research, 38(2):e10, pp. 1-9.

Extended European Search Report issued in European Application No. 21760040.2, date of mailing: Mar. 4, 2024, 11 pages.

Gan, 2014, A combined cell-free transcription-translation system from *Saccharomyces cerevisiae* for rapid and robust protein synthesis, Biotechnol, 9(5):641-651.

Jewett, 2004, Mimicking the *Escherichia coli* cytoplasmic environment activates long-lived and efficient cell-free protein synthesis, Biotechnol Bioeng, 86(1):19-26.

Kelwick, 2016, Development of a Bacillus subtilis cell-free transcription-translation system for prototyping regulatory elements, Metab Eng 38:370-381.

Kigawa, 1999, Cell-free production and stable-isotope labeling of milligram quantities of proteins, FEBS Letters 442 (1):15-19.

Kim, 2001, Regeneration of adenosine triphosphate from glycolytic intermediates for cell-free protein synthesis, Biotechnol Bioeng, 74(4):309-316.

Needleman, 1970, A general method applicable to the search for similarities in the amino acid sequence of two proteins, J Mol Biol 48:443.

Niederholtmeyer, 2015, Rapid cell-free forward ngineering of novel genetic ring oscillators, eLife 4:e09771, 18 pages.

Opgenorth, 2014, A synthetic biochemistry molecular purge valve module that maintains redox balance, Nature Communications 5(4113):998.

Popova, 2015, A Robust and Versatile Method of Combinatorial Chemical Synthesis of Gene Libraries via Hierarchial Assembly of Partially Randomized Modules, PLOS ONE, 10(9):e0136778, 27 pages.

Ramachandran, 2004, Self-assembling protein microarays, Science, American Association for the Advancement of Science, 305(5680):86-90.

Shin, 2012, An *E. coli*Cell-Free Expression Toolbox: Application to Synthetic Gene Circuits and Artificial Cells, ACS Synth Biol, 1(1):29-41.

Sun, 2013, Protocols for Implementing an *Escherichia coli* Based TX-TL Cell-Free Expression System for Synthetic Biology, Journal of Visualized Experiments, 79(e50762), 14 pages.

Takahashi, 2015, Characterizing and prototyping genetic networks with cell-free transcription-translation reactions, Methods, 86:60-72.

Thompson, 1984, Coupled transcription—translation in extracts of Streptomyces lividans, Molecular and General Genetics MGG 195(−2):39-43.

* cited by examiner

SEQUENCE LISTING

```
<160> NUMBER OF SEQ ID NOS: 4

<210> SEQ ID NO 1
```

<211> LENGTH: 3540
<212> TYPE: DNA
<213> ORGANISM: Unknown
<220> FEATURE:
<223> OTHER INFORMATION: synthetic

<400> SEQUENCE: 1
atggacaata atcccaatat caatgagtgt atcccttaca attgtttatc gaatcctgag 60
gttgaggtct taggtggtga gcgtatcgag acaggataca ctcccatcga catctccctg 120
tcattgactc aattcttact tagtgagttc gttccaggtg cgggtttcgt attgggtttg 180
gttgacatca tctggggcat cttcggtcca tctcaatggg acgcattctt agttcaaatc 240
gagcaattaa tcaatcaacg tatcgaggag ttcgcacgta atcaagcgat cagtcgtttg 300
gaaggtcttt caaatttata ccaaatctac gcagagtcgt tccgtgagtg ggaagcggac 360
ccaacgaatc ccgctttacg tgaggagatg cgtatccaat tcaatgacat gaatagtgca 420
ttaactactg caatcccttt gttcgctgtt caaaattacc aagtaccatt attgtcggta 480
tacgtccaag cagcgaatct tcacttatct gttcttcgtg acgtttccgt attcgggcaa 540
cgttggggtt tcgacgcggc gacgatcaat tcgcgttaca atgacttgac tcgtcttatc 600
ggaaattaca cggactacgc agtccgttgg tacaatacag gacttgagcg tgtatggggt 660
cctgacagtc gtgactgggt tcgttacaat caattccgtc gtgagttgac gcttactgtc 720
ttagacatcg ttgcactctt ccctaattac gactcgcgtc gttaccccat ccgtactgtt 780
tcacaattaa cgcgtgagat ctacacaaat ccagtcctcg agaatttcga cggttccttc 840
cgtggatcgg ctcaaggtat cgagcgttca atccgtagtc cacacttgat ggacatctta 900
aattcaatca cgatctacac tgacgcacac cgtggttact actactggtc gggtcaccaa 960
atcatggcgt cacctgttgg tttctcaggt cctgagttca cgttcccctt atacggtacg 1020
atgggaaatg cagcgcctca acaacgtatc gtcgcgcaac ttggtcaagg agtataccgt 1080
acattatcgt ctacattata ccgtcgtcct ttcaatatcg gtatcaataa tcaacaattg 1140
agtgtccttg acggtacgga gttcgcgtac ggtacttcga gtaatcttcc tagtgcggtt 1200
taccgtaagt ctgggacagt agactcgttg gacgagatcc cgccccaaaa taataatgta 1260
ccaccacgtc aaggattcag tcaccgtttg tcacacgtat cgatgttccg ttccggtttc 1320
tcgaattctt ccgtttcgat catccgtgca cctatgttct cttggatcca ccgttcggcg 1380
gagttcaata atatcatcgc gtccgactcc atcactcaaa tccctgctgt aaagggaaat 1440
ttcttattca atggttcagt catctcaggg cccggtttca ctggtggtga cttagtccgt 1500
ttgaattcga gtgggaataa tatccaaaat cgtgggtaca tcgaggttcc aatccacttc 1560
cccagtacaa gtactcgtta ccgtgtccgt gtacgttacg cgtccgtcac gcccatccac 1620
ttgaatgtta attggggcaa ttcgtcgatc ttctcgaata cagtccctgc aacggcaacg 1680
agtttagaca atttgcaatc cagcgacttc ggttacttcg agtctgcgaa tgcgttcaca 1740
tcttctcttg ggaatatcgt cggtgtccgt aatttctctg ggactgctgg tgtcatcatc 1800
gaccgtttcg agttcatccc cgtcactgcg acgcttgagg cggagtacaa tttagagcgt 1860
gcacaaaagg cggtaaatgc cctcttcacg tcaacaaatc aattaggatt aaagacgaat 1920
gtaacagact accacatcga ccaagtctcg aatcttgtta cttacctttc cgacgagttc 1980
tgtttggacg agaagcgtga gttgtctgag aaggtcaagc acgcgaagcg tttatcagac 2040
gagcgtaatt tgctccaaga ctctaatttc aaggacatca atcgtcaacc tgagcgtggg 2100
tggggtggtt ccactggtat cacgatccaa ggtggtgacg acgtctttaa agagaattac 2160
gtcacactta gtgggacatt cgacgagtgt taccccacat acctttacca aaagatcgac 2220
gagtccaagt tgaaggcgtt cactcgttac caattgcgtg gttacatcga ggactctcaa 2280
gaccttgaga tctaccttat ccgttacaat gcaaagcacg agacagtcaa tgtacccgga 2340
acagggtcgc tttggcccct ttctgcgcaa tcaccaatcg gaaagtgtgg tgagccaaat 2400
cgttgtgcgc ctcacttgga gtggaatcca gacctcgact gttcctgtcg tgacggtgag 2460
aagtgtgcac accactccca ccacttctcc cttgacatcg acgtaggatg tacggacttg 2520
aatgaggact tgggagtatg ggttatcttc aagatcaaga cacaagacgg tcacgcgcgt 2580
cttgggaatc ttgagttcct cgaggagaag ccacttgttg gtgaggcatt ggcacgtgtc 2640
aagcgtgcgg agaagaagtg gcgtgacaag cgtgagaagt tggagtggga aacgaatatc 2700
gtttacaagg aagcaaagga gtcggtagac gctttgttcg ttaattcaca atacgaccaa 2760
cttcaagcgg acacgaatat cgctatgatc cacgcagcgg acaagcgtgt tcactcgatc 2820
cgtgaggcat acttaccaga gttgtcggtt atccccggtg ttaatgcggc aatcttcgag 2880
gagctcgagg ggcgtatctt cacggcgttc tctctctacg acgcacgtaa tgtaatcaag 2940
aatggagact tcaataatgg tctttcatgt tggaatgtta agggacacgt agacgtcgag 3000
gagcaaaata atcaacgttc agttttggtt gtaccagagt gggaagccga ggttagtcaa 3060
gaggtccgtg tttgtcctgg tcgtggttac atccttcgtg taacagcata caaggaaggt 3120
tacggtgagg gatgtgttac aatccacgag atcgagaata atacagacga gttgaagttc 3180
tcaaattgtg ttgaggaaga gatctacccc aataatactg tcacatgtaa tgactacaca 3240
gtcaatcaag aggagtacgg tggagcttac acttcacgta atcgtggtta caatgaggcg 3300
ccatctgtac ccgcagacta cgcgtcagtt tacgaggaga agtcatacac agacggacgt 3360
cgtgagaatc cttgtgagtt caatcgtggg taccgtgact acactccttt acctgttggg 3420
tacgttacaa aggagttgga gtacttcccc gagactgaca aggtatggat cgagatcggt 3480
gagactgagg ggactttcat cgttgactcg gtcgagttat tattaatgga agagggttga 3540

<210> SEQ ID NO 2
<211> LENGTH: 7170
<212> TYPE: DNA
<213> ORGANISM: Unknown
<220> FEATURE:
<223> OTHER INFORMATION: synthetic

<400> SEQUENCE: 2
atgccctcga attcttacca atcgctttta gcatcagcac aagcgacttt caaggagatg 60
aagtcaaagc caaagatcca aatgttaatc caagagatca agaagggttt ccgtgagaat 120
ggtcgtaagt ggtcacccca actcttacaa caacaaaaga ctttagagca aacactcgag 180
gggaatgcgt accgtcgtta ctccaatgac cgtcccgttg gtatcagttc gctcgacaag 240
tcggagcaac aagcattcgt tggttacatc aaggctttag caactcgtgc aactacggtc 300
gacatccttg tccaagggaa tgaaaagact gcattagcat cgcaaacgga cgacgcgtta 360
ggtaatgcgg aagcgttccg tatgcttccc aaggacttcg cacaacgtta cggtgcgcgt 420
ggtaagcttg gggcacgcct cacgatcaat gtatctaagg ttcacttcaa tgtattggcg 480
cgtgcgttga cacaactttt caatgacgac aatcgtgggt ggctcgagca agcgaagatc 540
atgggtccaa agaatctcgg ttcgcgtaca gaccaagcgg ttatctacct ctcacgtgca 600
ggtatcgagc acgctcaaac tatcggtaag aagcttaatg agctgctccc agcaacggca 660

-continued

```
ttcgtcgagc acacgccaac aggaatgtac cgtgtcggaa agggtatctc atactccgag    720
acagctgcgg gtggatcatc ttcgcacggt caatcgcgtg cgcaattgat cgcagcagca    780
ggaacgcact cacttttaac tgacatccct atcgagaagg cgttagctca cacgttgcaa    840
acacgtggtt acgacgttca caatcccgcg ctcttaagtc aagctctccg tgacagtgag    900
ttaaagggtg agctcgtacc catgaatggt ggttccgagc ctcgtcgtgg atccgcggac    960
atccaccaat tcgcagcaaa tcctgttctc ttcgcgaagt caaatacgat caatgctgag   1020
acactcatcc gttcgggatc acttccagcc gaggggaatg cgttattagt aaagatcggt   1080
tcgggtcttt acgagctcga ctacacggac cgtaatgcga ataatgacgt tgctgccgag   1140
ggagcgaatt ctatgcccgc gtacttcctt gggtacgact ctacggacca agcgaatgcg   1200
tcgcctgcat acgtagacat ccccaagcac gcgatcgcag gttcattctt attcacaggg   1260
acattatcag gtggatctgt agtagtcacg tcattggacg cgaatactta ccgtgtttac   1320
cacgacggtc gtgttaatag ttcattgctt tacgacaatg ttgttatggc ggtagactac   1380
aaggactacc aagcggcggc aacgacagag aatcttgcag ttgcgtacat gcaatacgtc   1440
aatgaccaat ggcaattagc actccaacgt caagagtacc aacaagacgg tcaaacgtta   1500
cgtcttaagt tgcgtggtga cgaggagccc ttgagtatcc aaatcgctga ctcgcaagtc   1560
atcgagcgta atcaagcaca attcgcaact taccgtgagg agatccacca acgtcttaag   1620
aaggtcgcag cgcaattcgg tgtctccgtc gagggaatcg cagactcagt atacaccgag   1680
ggtgagttca gtcctgacca ccccgcgatc gcggcgtgga cgaagttacg tactgaggtc   1740
tacgaccgta tcaatgcgga cacaaagcaa cttgctgaca agcgtgacaa gctctacgag   1800
gagcgtcgta catcctcacg tcacgactta atcgaccaac aaatcaagca aatcaatatc   1860
acattggagt actacaaggc gcaatacgac acggtacttc gtgaggcagg gttcgttgag   1920
caatcgtggt tgtggcaaca aatcaagtcc cgtgacggta tggcagcagt cgtacgtatc   1980
gacaatactt caatgcaaaa tagtggtcct gagcacacgt cgagtgtagg tgagcgttac   2040
gctatcgcgg aagcgcacca acacaatgta cacggtacgg cgttcactaa tgggcaacgt   2100
cacttccgtg acatcaatat ccctggttta tacgaccgta tgagtgcact cgagatgaag   2160
tccttattct taaaggggca attgacgcca gagcaacaag ggctctcag tgtccacatc    2220
acagagacat cacaagctga gtacatcgac aaggttttaa agtggactgc ggtatactcg   2280
gaagatttcc accgtgcagg atcgtctttc gaccgtttag ctcctcaaga cttctactta   2340
tcgttggttg gtgacaagtc tggtggtcgt tgttacccat tggttcgtgc aatggcagtt   2400
gcgttggcga ataatgggga aacgggtatc aattccctcg tagagaagct tttccttgca   2460
gcagctgacc cccacgcgtc gtcgtctacg cttttaacga attctttgat ccgtttacac   2520
tcaaataatg ttgaggcggt acaagcgtca acggctcgtg ggcaagttaa gctctctgag   2580
gtagtttcgt tgttaaaggg agcgacgaaa acgtcaatgt tcgcacttaa tactcccaat   2640
cactcaatga tggtaggtaa tacgatcggt cttgagggac gtcgttacta cttctacgac   2700
ccaaatgttg gtatcttcgc attcaatgac gcagtttcat tcttccgtgc aatgaagaat   2760
caccttgtcg gtcgtaagtt agcggctcac tacggaagtc caggtggtga gttaactccc   2820
atcttcaatc ttgtcgagat cgacactggt aagatggcga aggttcccgt cggaaatgac   2880
ttgaatgttg cggaccttac gcgtcccgac gagctcacta cggttatcga gcaacgtcgt   2940
caagtcgagc aagcggttaa tgcgcaagtt cgtatcgcga aggacgctcg tttacacacg   3000
gctttagcaa cacttgacgc ggagcaatgg ggtgagaagt tcgcggaagc gtctactcgt   3060
```

```
ttaagtcaag agaataattt agaccaacgt tggatgcccg ttatcagtaa taccgaggac   3120
caaggtgagg gacgttacca aatccaattc atcaatcgtg cgcaacctga ggagacacgt   3180
tgggttagtt cgggcgacac tacgttcatc gagttccgtc gtttcgtcga cgagcacatg   3240
ttgacgctct cccaacactt cacgttcgag cacggacaaa tccgtcccaa gagtggtatc   3300
agtgaggcgg cgcctgtcga cggctcaat gcgggtttcg cgatccaaac attgatccaa    3360
tggttcgcgg acaagaatcg taatgacgca gcacgtggta tcgcgagtcc cgacctcgcg   3420
acggcattaa aggtccacag ttacctcaat ttcgtacaaa tggcgcacgg tggtgtacaa   3480
gacgtcacga agatcactgc attagtccgt acggctttgc gtggagaggt catggcagcg   3540
gagacatcgt taaaggactt cacatctatc ctcggacaca ctgttaatga gggagcgggt   3600
gtattgttcg gtggagcgat ggttggtttg gacgcgtacg agttagcgca cgcggagaat   3660
gacgttcaaa aggcggtttt cggtacacaa ttggcgttcg actcggcatc cttcgtcaca   3720
ggtactgcag gagttggagc aggtctgatg ggtgcaagta ctgcgggtgc ggtcttaggt   3780
ggagcagggg tcatccttgg cggtttagcg gtcgggttca ctgctcttgc gcaagcgttc   3840
ggggcagttg cagaggacgc aaaggcagtt ggtcgttact tcaatacgtt agacgacgct   3900
tacaagggta atggttaccg ttacgacaat gagaagaagg ttttagtccc tttacctgga   3960
gcagtaatca agactttaga cttacgtaag aatcaaatcg acttcgactc ccaatacatc   4020
taccgtacgc actcaggttc gacggggtct ggacgtatca attacttctt ctggatcggt   4080
gacttcccaa agatggttca cgaccgtagt caagcgatcg aggtccgttc aggaatcggt   4140
tacaaggacg catcgcgttc actcgagcac ggggacagta atgtagtcat cttgccaggt   4200
acgcctaagt catacatcaa ttacgagtac atgcaattac ctggggcgac tacacgtcac   4260
gacgcgggtt tcgacgtcat ccgtcgtctt gaagaggaca agcgtttcga ctacgacttc   4320
tacatcttcc ctggggaagt tactatccgt cgtatccacc aagagtacgt tgcgacacct   4380
atcgaggtaa tgttagacca acgtaatcgt caacttatcg tacccgagtt gcctaaggaa   4440
ttgcacggtt acttacacta cgagatcaaa ggggcgggtg gtgagtacct tatcggttta   4500
aatgagggga cgtcggtaaa gttaacgtca gacgcacctc acaatcttgt aggttcgacg   4560
ccctcgcact ggatcatcga ctctagtcaa ttggcaggtg actctatctc agtctcaaag   4620
aatcgtctta ctgttggcgg tgtagtagtc gagttagact ccgaccgcaa ggagcaagtt   4680
cttgttgtca atcgtaaggg tgaggttcgt gaggttgact tcgcgtccct tacggcgcaa   4740
gtcgtcagcg aggacgcgag taagtggcaa gttcctggtc aacaaatcga gcaacacctc   4800
aatgaccttg caaaggcgca ccaactccac ggtcaatacg ttgtagttga gaattactca   4860
cacaatggtc gtgacgtagg tcgtgcgttc tacgacgtta ctaataagcg tatgttgttc   4920
actgacacga cacacgagca aacgaagcac gctcaacttg gagcagtaat ggggaatcac   4980
gcgtacttct acgacgcgga caatgctgca gcttggcgtg ttgacatcgc tactggtcaa   5040
atcgacgctc aattcgagcc atggttcaat caatcagcgg gtcaaatctc tcgtttatgg   5100
caagagggtg acgcagtcta cctcgcgcgt cgttaccaac tcaaggggaa agaggcggag   5160
ctttcctacc gtttattggg cgaccgtatg gagttagttt cggcagtagg tgacgacgct   5220
ctccttcaat tgtccgcacg tactgggcgt cacggtgacg agttgaaaac gatcttacaa   5280
gggtacgagt ctaattcgac tcaacgtgag acaccaacgt acatgttagg agcgcgttta   5340
atccaaccaa cgtcggcggc gttagttaca gtctttggtg tagacacagc tggagttgcg   5400
```

caccgttact ggatccgtac atcagacggt acgttgatca agcctaattt agcaccacca 5460
gctgactgga ctttacactt cgaggctcac gagcaaacac gttcggcatg gcccatccca 5520
gcggaccttg ttctcgcggg ttcgatccct cgtcctgcgg gtaccgaggt tttcttcttc 5580
tactcaaagg agcaaaaggc gcttttccgt caagaggggc ctgggcaaac tgtcttagac 5640
gcgaatcacc cctcggcgtt acgtatctcc actcctgagc ttgcaaattt ggtaaatttg 5700
aatggatcat tacttgcaat cactgaggac gggcgtgttg cgcgtcttga cgcgcaagga 5760
caattgaatt acgaggcagt taatgagcac tggttgaagg gacgtacaca ctggtggcgt 5820
gacctcgcta atatcacgga cacgacgact ttagcagtat tcgggatcaa gggtagtgac 5880
ggtaagtctc ttctccccgt atggtaccac aatggtcaag ttgtcgttgc gtccgcagcg 5940
ttgtcagaca agtctcttca attcttaggt ttcgagatgg acgggacgtc ggcgcgttta 6000
ttcgagcccg agtctgggaa gctctaccgt caacccgcaa tgacggctaa tgctcttgcg 6060
gcggctttcg gagcggacca agttttagac gactctgcgc aattacccgc tgcaagtgag 6120
ttgacacctg agttacacct caagtctgca caacaagttg acgtaggtat gcgtttaatc 6180
actgtcaagg gtgagatctt gctccgtact aataatggtg agctccaatt ggttggtgtc 6240
gacaaggggt ggcaacaaaa taatcttgcg caattgtcgc aagcgctcac aaagctcgcg 6300
gaccaatggc aagcaaaggg aatcttaacg ttgcaagaca ataaagagcc tggttggttc 6360
gacatcggaa gtggacaagt tttctcaggt aatggaatcc ccgtatccga caatttgcgt 6420
ttcgttggta tcgcagctgg ggagaaggca gcttacgtat actcgcctac gactcaagcg 6480
ctctaccaaa tcaaggacgg gaatgcgcaa atgcttaata agttcacagg tgtcgagcgt 6540
atcggatcaa gtttactctt acaaggtggt ggtgttggcg gtagtaagga cgacttaact 6600
ccgcccatca tcgctggggt agacagtgtc gtactccacg gtggggcgga cgacgacacg 6660
taccgtttaa ataaggcaat gtggagtcac taccgtacgg taatcatcga caatgacgac 6720
cgtggtcaag cgcttgaccg tcttattctc ccattagcgg actcggagtc catcttggta 6780
aatcgtcacg acgacgacct tgtccttacg gactcaagta atggtactgc tttggttgta 6840
cgtcaagttt tcggttctca agcaatggcg taccgtcatc tccaaatcga gcttgagggt 6900
tcgtcaagtg taatcaatgt tgaccacctc gtagagggtt tcacgcgtcg tagttacact 6960
aaagagggtt tgatggagtt gtcatgggcg tctaatcaac cagtaatcac gactcacgca 7020
gttgacgcag ttccaggtgc agagcgtcct aatttggcga agctctctgg agcgatggca 7080
tccttccctg acacgggtgg tgcacgtgag caccttccac aaatccgtca agcatcgctc 7140
agtgtccttg ttagtagttt gtctggttga 7170

<210> SEQ ID NO 3
<211> LENGTH: 678
<212> TYPE: DNA
<213> ORGANISM: Unknown
<220> FEATURE:
<223> OTHER INFORMATION: synthetic

<400> SEQUENCE: 3
atggagcttt tcactggcgt tgttcccatc ctggtcgagc tggacggcga cgtaaacggc 60
cacaagttca gcgtgtccgg cgagggcgag ggcgatgcca cctacggcaa gctgaccctg 120
aagttcatct gcaccaccgg caagctgccc gtgccctggc ccaccctcgt gaccaccctg 180
acctacggcg tgcagtgctt cagccgctac cccgaccaca tgaagcagca cgacttcttc 240
aagtccgcca tgcccgaagg ctacgtccag gagcgcacca tcttcttcaa ggacgacggc 300

```
aactacaaga cccgcgccga ggtgaagttc gagggcgaca ccctggtgaa ccgcatcgag    360

ctgaagggca tcgacttcaa ggaggacggc aacatcctgg ggcacaagct ggagtacaac    420

tacaacagcc acaacgtcta tatcatggcc gacaagcaga agaacggcat caaggtgaac    480

ttcaagatcc gccacaacat cgaggacggc agcgtgcagc tcgccgacca ctaccagcag    540

aacaccccca tcggcgacgg ccccgtgctg ctgcccgaca accactacct gagcacccag    600

tccgccctga gcaaagaccc caacgagaag cgcgatcaca tggtcctgct ggagttcgtg    660

accgccgccg ggatctaa                                                  678
```

<210> SEQ ID NO 4
<211> LENGTH: 7554
<212> TYPE: DNA
<213> ORGANISM: Unknown
<220> FEATURE:
<223> OTHER INFORMATION: synthetic

<400> SEQUENCE: 4

```
atgaatgagt ccgttaaaga gatccccgac gttcttaagt cacaatgtgg tttcaattgt     60

ctcactgaca tctctcactc atcgttcaat gagttccgtc aacaagtctc cgagcacctc    120

tcttggagtg aaacgcacga cctttaccac gacgcgcaac aagcgcaaaa ggacaatcgc    180

ctctacgagg cgcgtatctt gaagcgtgca aatccccaac ttcaaaatgc ggtacacttg    240

gcgatcttag ctccaaatgc ggagctcatc ggatacaata atcaattcag tggtcgtgct    300

tcacaatacg tagcaccagg tacggtatcc tcgatgttct cacctgcggc ataccttact    360

gagttgtacc gtgaggcgcg taatcttcac gcatcagact cagtatacta cttagacacg    420

cgtcgtcctg acttgaagtc gatgacttta tcccaacaaa atatggacac ggagttgtca    480

actctttcct tatcgaatga gttactcttg gagaatatca agacggagtc gaagttagag    540

aattacacga aggttatgga gatgttgtca acgttccgtc catccggggc gacgccctac    600

cacgacgcat acgagaatgt ccgtgaggta atccaacttc aagacccagg gttggagcaa    660

ctcaatgcgt cccccgcgat cgcgggtttg atgcaccaag catcgcttct cggtatcaat    720

gcatcaatct caccagagtt attcaatatc ctcactgagg agatcaccga gggtaatgcg    780

gaagagttct acaagaagaa tttcggtaat atcgagcccg catccttggc gatgcctgag    840

tacctcaagc gttactacaa tcttagtgac gaggagttaa gtcaattcat cgggaaggca    900

tctaatttcg ggcaacaaaa gtactcaaat aatcaattaa tcacgcctgt tgttaattca    960

tctgacggta cggtaaaggt ttaccgtatc actcgtgagt acacaacaaa tgcataccaa   1020

gtagacttgg agcttttccc attcggcgga gagaattacc gtttggacta caagttcaag   1080

gactcccgtg acgtttccta cttatctatc aagctcaatg acaagcgtga gcttgtacgt   1140

actgaggacg cgccccaagt caatatcgag tacagtgcaa atatcacgct ttcaacaaca   1200

gacatctcgc aacctttcga gatcggttta acgcgtgtat acccttccag ttcctgggct   1260

tacgcagcgg cgaagttcac ggtcgaggag tacaatcaat acagtttcct tctcaagctt   1320

aataaggcta tccgtctttc gcgtgcaacg gagcttagtc caactatcct tgagggaatc   1380

gtccgttcgg taaatccaca attagacatc aatactgagg tcttggggaa ggttttcttg   1440

acaaagtact acatgcaacg ttacgcaatc aatgcggaaa cggcattaat cttgtgtaat   1500

gcgccaatct cgcaacgttc gtacgacaat caaccctcgc aattcgaccg tctgttcaat   1560

acgcccttac ttaatgggca atacttctcc acgggtgacg aggagatcga cttgaattca   1620
```

ggttccacag gagactggcg taagacggtc cttaagcgtg cgttcaatat cgacgacgtt 1680
tcgctttacc gccttcttaa gatcacagac cacgacaata aggacgggaa gatcaagaat 1740
aatttgaaga atttatcgaa tttgtacatc ggtaagcttc ttgcggacat ccaccaactc 1800
acaatcgacg agttagacct tctcctcgta gcagttggag agggtaagac aaatctctcg 1860
gcaatctcgg acaagcaact tgcgacgttg ttgcgtaagt taaatacgat cactggttgg 1920
ttacacactc aaaagtggag tgtattccaa ctcttcatca tgacttccac gagttacaat 1980
aagacgttaa ctcctgagat caagaatctc ttagacactg tataccacgg attgcaagga 2040
ttcgacaagg acaaggctga gttattgcac gtcatggctc catacatcgc ggcaacttta 2100
caactttcct cggagaatgt cgcgcacagt gtattacttt gggcagacaa gctccaaccc 2160
ggagatggtg cgatgactgc agagaagttc tgggactggt taaatacgaa gtacacaccc 2220
ggatcatcgg aagcggttga aacgcaagag cacatcgttc aatactgtca agcattggct 2280
caactcgaga tggtttacca ctctacgggt atcaatgaga atgcgttccg tctgttcgtt 2340
acgaagcctg agatgttcgg agcggcgact ggggcagcac ctgcgcacga cgcactctct 2400
ttgatcatgc tcacgcgttt cgctgactgg gtaaatgcgc ttggtgagaa ggcttcgtca 2460
gtacttgcgg cgttcgaggc aaattcactt acagcggagc aattggcgga cgctatgaat 2520
ttggacgcga atctccttct tcaagcatct acgcaagctc aaaatcacca acatctccca 2580
cccgttacac ctgagaatgc gttctcgtgt tggacttcga tcgacacgat ccttcaatgg 2640
gtcaatgtcg cgcaacaatt gaatgtcgcg ccccaaggag tttcggcgtt ggtcggatta 2700
gactacatcc aatcgatgaa ggagacaccc acgtacgcac aatgggagaa tgcggcgggt 2760
gttttgacgg cggggcttaa ttcgcaacaa gcgaatacgt tgcacgcgtt cttggacgag 2820
tctcgtagtg cagcgcttag tacttactac atccgtcaag tagcaaaggc agcagctgca 2880
atcaagtctc gtgacgactt ataccaatac cttcttatcg acaatcaagt ttcggctgcg 2940
atcaagacta cgcgtatcgc cgaggcgatc gcgtccatcc aactttacgt taatcgtgca 3000
ctcgagaatg tcgaggagaa tgcgaattca ggtgtcatct cacgtcaatt cttcatcgac 3060
tgggacaagt acaataagcg ttactctacg tgggcaggag tatctcaact cgtttactac 3120
cccgagaatt acatcgaccc aacgatgcgt atcggacaaa cgaagatgat ggacgcgctc 3180
cttcaatcag ttagtcaatc acaactcaat gcggacactg tcgaggacgc gttcatgtcg 3240
tacctcacgt cgttcgagca agttgcaaat ctcaaggtca tcagtgcgta ccacgacaat 3300
atcaataatg accaaggact cacttacttc atcggtcttt cagaaacgga cgctggtgag 3360
tactactggc gtagtgtaga ccacagtaag ttcaatgacg gtaagttcgc tgcgaatgca 3420
tggtcggagt ggcacaagat cgactgtcca atcaatccct acaagtcgac tatccgtcct 3480
gtaatctaca agtcccgttt gtacctctta tggcttgagc aaaaggagat cacgaagcaa 3540
acagggaatt caaaggacgg gtaccaaaca gaaacggact accgttacga gcttaagctt 3600
gcacacatcc gttacgactc gacatggaat acgcctatca cattcgacgt taatgagaag 3660
atcagtgagt taaagttaga gaagaatcgt gcacccggat tgtactgtgc gggataccaa 3720
ggtgaggaca cgcttttggt catgttctac aatcaacaag acactcttga ctcgtacaag 3780
aatgcgtcga tgcaaggttt atacatcttc gctgacatgg tttcaaagga catgactcca 3840
gagcaatcga atgtttaccg tgacaattcc taccaacaat tcgacactaa taatgttcgt 3900
cgtgtcaata atcgttacgc ggagaattac gagatccctt catcagtatc atctcgtaag 3960
gactacggtt ggggcgacta ctacttatca atggtttaca atggtgacat ccccacaatc 4020

```
aattacaagg cagcatcttc ggaccttaag atctacatca gtccaaagtt acgtatcatc   4080
cacaatgggt acgagggtca acaacgtaat caatgtaatt taatgaataa gtacggaaag   4140
ctcggggaca agttcatcgt ctacacaagt ctcggggtca atccaaataa ttcttcgaat   4200
aagttgatgt tctaccccgt ctaccaatac tctgggaata ctagtggatt gaatcaaggg   4260
cgtttattgt tccaccgtga cacgacatac ccttctaagg ttgaggcttg gatccccggt   4320
gcaaagcgtt ccttaacgaa tcaaaatgca gctatcggtg acgactacgc aactgactct   4380
ttaaataagc cagacgactt aaagcaatac atcttcatga ctgactccaa ggggactgcg   4440
acggacgtat ctgggcctgt agagatcaat acggcgatct cccctgctaa ggtacaaatc   4500
atcgttaagg cgggcggaaa ggagcaaacg ttcactgcag acaaggacgt ttctatccaa   4560
ccctcgcctt cgttcgacga gatgaattac caattcaatg ctcttgagat cgacggttcc   4620
ggactcaatt tcatcaataa ttcggcgtcg atcgacgtaa cattcacggc attcgcagag   4680
gacgggcgta agctcggtta cgagtcattc agtatccccg tcactttaaa ggtttcaaca   4740
gacaatgcgc tcacgttaca ccacaatgag aatggggctc aatacatgca atggcaatcc   4800
taccgtacac gtttaaatac gttattcgct cgtcaacttg ttgctcgtgc gacgacgggt   4860
atcgacacta tcctctctat ggagactcaa aatatccaag agcctcaatt gggtaagggt   4920
ttctacgcga ctttcgtcat cccgccatac aatctctcta cacacggtga cgagcgttgg   4980
ttcaagctct acatcaagca cgtcgtcgac aataatagtc acatcatcta ctcaggtcaa   5040
ttaacagaca cgaatatcaa tatcactttg ttcatccccc ttgacgacgt ccccccttaat   5100
caagactacc acgcgaaggt atacatgact ttcaagaagt caccttcgga cggtacgtgg   5160
tggggtcctc acttcgttcg tgacgacaag ggtatcgtta ctatcaatcc taagtcaatc   5220
ctcactcact tcgagagtgt aaatgtttta aataatatca gttcagagcc tatggacttc   5280
tctggagcaa attcattata cttctgggag ttattctact acacacccat gcttgtcgca   5340
caacgtttat tacacgagca aaatttcgac gaggcgaatc gttggttaaa gtacgtctgg   5400
tcacccagtg gttacatcgt tcacggacaa atccaaaatt accaatggaa tgtacgtcca   5460
ctcttagagg acacgtcatg gaatagtaat ccattagact ccgttgaccc tgacgcggtc   5520
gcacaacacg accccatgca ctacaaggtt tccactttca tgcgtacgct cgacttatta   5580
atcgcacgtg gtgaccacgc ataccgtcaa cttgagcgtg acacgttaaa tgaggcaaag   5640
atgtggtaca tgcaagccct tcacctgctc ggagacaagc cctacttacc actttccacg   5700
acgtggagtg accctcgtct tgaccgtgca gcagacatca cgactcaaaa tgctcacgct   5760
tctgcgatcg tcgctttacg tcaaaatatc cccacacctg ctcccttgtc cttacgttcg   5820
gcgaatacgt taacagactt gttcctgccc caaatcaatg aggttatgat gaattactgg   5880
caaacgttgg cacaacgtgt ttacaattta cgtcacaatt tgtcgatcga cggtcaacca   5940
ctctacttgc ctatctacgc ggcgccagcg gaccctaagg cattattatc ggcagcggtc   6000
gcgacgagtc aaggaggagg gaagttgccc gagtccttca tgtccttatg gcgtttccct   6060
cacatgcttg agaatgcgcg tgggatggtt tctcaattga cgcaattcgg gtcaacgtta   6120
caaaatatca tcgagcgtca agacgcagag gcgttgaatg ctctccttca aaatcaagcg   6180
gcggagctca tcctcacgaa tctctccatc caagacaaga cgatcgagga gcttgacgca   6240
gagaaaactg tccttgagaa gagtaaggca ggagcgcaat cgcgtttcga ctcgtacggt   6300
aagttatacg acgagaatat caatgctggt gagaatcaag cgatgacatt gcgtgcgagt   6360
```

-continued

| | |
|---|---|
| gcagcaggtc ttactactgc agtacaagct tcgcgtttgg caggagcggc agcagactta | 6420 |
| gttcctaata tcttcggttt cgcgggtggt gggtcacgtt ggggtgcaat cgcggaagca | 6480 |
| actgggtacg tcatggagtt ctcggcgaat gtcatgaata ctgaggcaga caagatctcg | 6540 |
| caatcagaaa cgtaccgtcg tcgtcgtcaa gagtgggaga tccaacgtaa taatgcggaa | 6600 |
| gcggagttaa agcaaatcga cgcgcaactc aagtcattag cagtccgtcg tgaggcagct | 6660 |
| gtcttacaaa agacatcctt aaagactcaa caagagcaaa cgcaatcgca attggcattc | 6720 |
| ttgcaacgta agttctcaaa tcaagcgctc tacaattggc ttcgtggtcg cctcgctgca | 6780 |
| atctacttcc aattctacga cttggcagtt gctcgttgtc ttatggctga gcaagcgtac | 6840 |
| cgttgggagc tcaatgacga ctcggcgcgt ttcatcaagc ccggggcatg gcaagggacg | 6900 |
| tacgcgggtt tgttggcagg tgagacatta atgcttagtt tagcgcaaat ggaagatgct | 6960 |
| cacttaaagc gtgacaagcg tgcgttagag gtcgagcgta cagtatcctt agcggaagta | 7020 |
| tacgcgggac tcccaaagga caatggacct ttctcgcttg cacaagagat cgacaagtta | 7080 |
| gttaataagg gttcgggttc agtcgggaat ggtagtaata atctcgcatt cggagcgggt | 7140 |
| tcagacacta agacttcgct tcaagcttct gtctcattag cggaccttaa gatccgtgag | 7200 |
| gactaccctg catcattagg aaagatccgt cgtatcaagc aaatctcagt tacacttcct | 7260 |
| gcgcttctcg gtccctacca agacgtacaa gcgatcttgt catacggtga caaggcgggt | 7320 |
| cttgcaaatg gttgtgaggc gcttgcggtc agtcacggta tgaatgactc aggacaattc | 7380 |
| caattagact tcaatgacgg taagttcctt cctttcgagg gaatcgcgat cgaccaaggg | 7440 |
| acgttaacgc tttccttccc caatgcgagt atgcccgaga agggtaagca agctactatg | 7500 |
| ctcaagacac ttaatgacat catcttgcac atccgttaca cgatcaaggg ttga | 7554 |

METHODS AND COMPOSITIONS FOR IDENTIFYING TRAITS USING A CELL-FREE SYSTEM

CROSS REFERENCE TO RELATED APPLICATIONS

This application is a national stage entry of PCT International Application No. PCT/US2021/020293, which claims priority to and the benefit of U.S. Provisional Application No. 62/983,007 filed Feb. 28, 2020, the entire disclosure of which is incorporated herein by reference.

SEQUENCE LISTING

The ASCII text file submitted on Mar. 1, 2021 via EFS-Web, entitled "011201seq.txt" created on Mar. 1, 2021, having a size of 25,378 bytes, is incorporated herein by reference in its entirety.

FIELD

Compositions and methods disclosed herein relate to utilizing in vitro transcription/translation (TXTL) systems for identification of desired traits from a library of candidates, such as agricultural traits.

BACKGROUND

There is extensive biological data encoded in DNA that is of unknown function. This data varies from naturally derived proteins, peptides, and molecular control components to semi-synthetic and engineered variants thereof. With the advent of high-throughput sequencing, as of 2017, more than 2.7 trillion bases of information are known, and only a small fraction are expressed. Tools that are able to determine the products of this DNA will be essential to understanding this information.

Separately, synthetic biology has emerged as an important field for which essential processes can be understood and engineered. Within this field there are both natural, semi-synthetic, and engineered genes, regulatory parts, and other components that are in need of testing.

Despite efforts and progresses, current approaches are limited to conduct high-throughput functional genomics to determine products from DNA and to promote synthetic biology approaches. Challenges still remain in developing engineering-driven approaches and systems to accelerate the design-build-test cycles required for reprogramming existing biological systems, constructing new biological systems and testing genetic circuits for transformative future applications in diverse areas including biology, engineering, green chemistry, agriculture and medicine.

An in vitro transcription-translation (TXTL) system (Shin & Noireaux 2012; Sun et al. 2013) has been developed which allows for the rapid prototyping of genetic constructs (Sun et al. 2014) in an environment that behaves similarly to a cell (Niederholtmeyer et al. 2015; Takahashi et al. 2015). One of the main purposes of working in vitro is to be able to generate fast speeds—in vitro, reactions can take 8 hours and can scale to thousands of reactions a day, a multi-fold improvement over similar reactions in cells (Sun et al. 2014).

Despite the production of this system, to date it has not been shown that the system can be used to directly identify of traits, especially those related to agriculture, by avoiding cellular heterologous expression.

SUMMARY

In one aspect, provided herein is a method for screening using an in vitro transcription/translation (TXTL) system, comprising: providing a library of genetic candidates to be screened, each genetic candidate encoding one or more protein of interest; expressing each genetic candidate in an in vitro transcription/translation (TXTL) system, thereby producing a plurality of compositions each comprising the one or more protein of interest; and subjecting the plurality of compositions to an assay for assessing a desired phenotype, thereby determining whether the one or more protein of interest exhibits the desired phenotype.

In some embodiments, the library comprises at least 2, at least 5, or at least 10 genetic candidates, preferably from about 5 to about 10,000 genetic candidates. In some embodiments, the library comprises a genome of an organism of interest. In some embodiments, the library comprises a plurality of homologs. In some embodiments, the library comprises a plurality of variants. In some embodiments, each genetic candidate is a gene or a genetic pathway comprising a plurality of genes. In some embodiments, each gene can be engineered to be under the control of the same promoter, preferably a constitutive promoter. In some embodiments, each genetic candidate comprises a linear DNA.

In some embodiments, the genetic candidates are variants having alternate codons encoding the same protein, and the library is used for codon optimization.

In some embodiments, the genetic candidates are variants encoding the same protein, and the library is used to identify internal translation sites.

In some embodiments, the genetic candidates are variants encoding the same protein, and the library is used to discover domain-shuffled variants.

In some embodiments, the genetic candidates are engineered genes having different genetic elements, and the library is used to identify optimal transcription and/or translation regulatory units.

In some embodiments, step (b) comprises substantially simultaneously expressing all genetic candidates.

In some embodiments, step (c) comprises substantially simultaneously subjecting the plurality of compositions to the assay.

In some embodiments, the assay comprises an organism such as an insect, a plant, an animal, or a bacterium. In some embodiments, the desired phenotype comprises death or growth of the organism. In some embodiments, the subjecting step comprises feeding or injecting each composition to the organism.

In some embodiments, the desired phenotype is selected from insecticide, herbicide, antibiotic, pesticide, crop protection, and/or seed trait (or variants thereof), so as to discover or characterize trait enhancement, crop enhancement or protective components, or microbes.

In some embodiments, the method does not comprise purifying or isolating the one or more protein of interest after step (b).

In some embodiments, the method is a high through-put screening method capable of screening at least 100, at least 500, at least 1,000, at least 10,000 genetic candidates per month.

In some embodiments, the method further includes comparing the plurality of compositions to one another to identify a final composition having a desired characteristic. In some embodiments, the desired characteristic comprises production amount, protein produced, mRNA produced, and/or a desired response against another product.

In some embodiments, the method further includes combining two or more compositions and testing for a desired response against another product.

In some embodiments, the method further includes purifying the one or more proteins of interest and subjecting the purified proteins to the assay.

Figure 1:
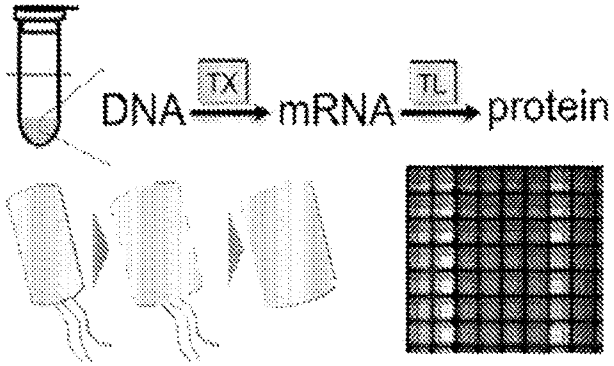
FIG. 1 provides an overview of cell-free expression. In cell-free expression, a host is converted into a lysate and supplied with factors to enable the conversion of DNA to mRNA and protein.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Disclosed herein are methods for utilizing cell-free transcription and translation reaction for identifying desired traits such as agricultural traits. In an embodiment, the products of a cell-free transcription and translation reaction can be directly used to identify a response reacting with a product. In another embodiment, multiple compositions of cell-free transcription and translation reactions can be compared against each other to identify an ideal composition. In another embodiment, the products of a cell-free transcription and translation reaction can be further purified and then used to identify a response against another product, or can be used to develop a new product that then has a response against another product.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

The articles "a" and "an" are used herein to refer to one or to more than one (i.e., at least one) of the grammatical object of the article. By way of example, "an element" means one element or more than one element.

As used herein, the term "about" means within 20%, more preferably within 10% and most preferably within 5%. The term "substantially" means more than 50%, preferably more than 80%, and most preferably more than 90% or 95%.

As used herein, "a plurality of" means more than 1, e.g., 2, 3, 4, 5, 6, 7, 8, 9, 10, 11, 12, 13, 14, 15, 16, 17, 18, 19, 20, or more, e.g., 25, 30, 40, 50, 60, 70, 80, 90, 100, 200, 300, 400, 500, or more, or any integer therebetween.

The term "additive" refers to an addition, whether chemical or biological in nature, whether natural or synthetic or, that is provided to a system. Examples include but are not limited to enzymes, oxidases, oxygenases, sugars, betaine, cyclodextrans, solvents, alcohols, proteins, enzymes, nucleic acids, organelles, mitochondria, and chloroplasts.

As used herein, the terms "nucleic acid," "nucleic acid molecule" and "polynucleotide" may be used interchangeably and include both single-stranded (ss) and double-stranded (ds) RNA, DNA and RNA: DNA hybrids. These terms are intended to include, but are not limited to, a polymeric form of nucleotides that may have various lengths, including deoxyribonucleotides and/or ribonucleotides, or analogs or modifications thereof. A nucleic acid molecule may encode a full-length polypeptide or RNA or a fragment of any length thereof, or may be non-coding.

Nucleic acids can be naturally-occurring or synthetic polymeric forms of nucleotides. The nucleic acid molecules of the present disclosure may be formed from naturally-occurring nucleotides, for example forming deoxyribonucleic acid (DNA) or ribonucleic acid (RNA) molecules. Alternatively, the naturally-occurring oligonucleotides may include structural modifications to alter their properties, such as in peptide nucleic acids (PNA) or in locked nucleic acids (LNA). The terms should be understood to include equivalents, analogs of either RNA or DNA made from nucleotide analogs and as applicable to the embodiment being described, single-stranded or double-stranded polynucleotides. Nucleotides useful in the disclosure include, for example, naturally-occurring nucleotides (for example, ribonucleotides or deoxyribonucleotides), or natural or synthetic modifications of nucleotides, or artificial bases. Modifications can also include phosphorothioated bases for increased stability.

As used herein, unless otherwise stated, the term "transcription" refers to the synthesis of RNA from a DNA template; the term "translation" refers to the synthesis of a polypeptide from an mRNA template. Translation in general is regulated by the sequence and structure of the 5' untranslated region (5'-UTR) of the mRNA transcript. One regulatory sequence is the ribosome binding site (RBS), which promotes efficient and accurate translation of mRNA. The prokaryotic RBS is the Shine-Dalgarno sequence, a purinerich sequence of 5'-UTR that is complementary to the UCCU core sequence of the 3'-end of 16S rRNA (located within the 30S small ribosomal subunit). Various Shine-Dalgarno sequences have been found in prokaryotic mRNAs and generally lie about 10 nucleotides upstream from the AUG start codon. Activity of a RBS can be influenced by the length and nucleotide composition of the spacer separating the RBS and the initiator AUG. In eukaryotes, the Kozak sequence lies within a short 5' untranslated region and directs translation of mRNA. An mRNA lacking the Kozak consensus sequence may also be translated efficiently in an in vitro system if it possesses a moderately long 5'-UTR that lacks stable secondary structure. While *E. coli* ribosome preferentially recognizes the Shine-Dalgarno sequence, eukaryotic ribosomes (such as those found in retic lysate) use the Kozak ribosomal binding site.

As used herein, the term "host" or "host cell" refers to any prokaryotic or eukaryotic single cell (e.g., yeast, bacterial, archaeal, etc.) cell or organism. The host cell can be a recipient of a replicable expression vector, cloning vector or any heterologous nucleic acid molecule. Host cells may be prokaryotic cells such as species of the genus *Escherichia* or *Lactobacillus*, or eukaryotic single cell organism such as yeast. The heterologous nucleic acid molecule may contain, but is not limited to, a sequence of interest, a transcriptional regulatory sequence (such as a promoter, enhancer, repressor, and the like) and/or an origin of replication. As used herein, the terms "host," "host cell," "recombinant host" and "recombinant host cell" may be used interchangeably. For examples of such hosts, see Green & Sambrook, 2012, Molecular Cloning: A laboratory manual, 4th ed., Cold Spring Harbor Laboratory Press, New York, which are hereby incorporated by reference herein in their entireties.

As used herein, the term "selectable marker" or "reporter" refers to a gene, operon, or protein that upon expression in a host cell or organism, can confer certain characteristics that can be relatively easily selected, identified and/or measured. Reporter genes are often used as an indication of whether a certain gene has been introduced into or expressed in the host cell or organism. Examples, without limitation, of commonly used reporters include: antibiotic resistance ("abR") genes, fluorescent proteins, auxotropic selection modules, β-galactosidase (encoded by the bacterial gene lacZ), luciferase (from lightning bugs), chloramphenicol acetyltransferase (CAT; from bacteria), GUS (β-glucuronidase; commonly used in plants) green fluorescent protein (GFP; from jelly fish), and red fluorescent protein (RFP). Typically host cells expressing the selectable marker are protected from a selective agent that is toxic or inhibitory to cell growth.

The term "engineer," "engineering" or "engineered," as used herein, refers to genetic manipulation or modification of biomolecules such as DNA, RNA and/or protein, or like technique commonly known in the biotechnology art.

As described herein, "genetic module" and "genetic element" may be used interchangeably and refer to any coding and/or non-coding nucleic acid sequence. Genetic modules may be operons, genes, gene fragments, promoters, exons, introns, regulatory sequences, tags, or any combination thereof. In some embodiments, a genetic module refers to one or more of coding sequence, promoter, terminator, untranslated region, ribosome binding site, polyadenylation tail, leader, signal sequence, vector and any combination of the foregoing. In certain embodiments, a genetic module can be a transcription unit as defined herein.

As used herein, the term "promoter" refers to a DNA sequence capable of controlling the transcription of a nucleotide sequence of interest into mRNA, and generally contains a RNA polymerase binding site and one or more operators and/or catabolite activator protein (also known as cyclic AMP receptor protein, "CAP") binding sites for biding of other transcriptional factors. A promoter may be constitutively active ("constitutive promoter") or be controlled by other factors such as a chemical, heat or light. The activity of an "inducible promoter" is induced by the presence or absence or biotic or abiotic factors. Aspects of the disclosure relate to an "autoinducible" or "autoinduction" system where an inducible promoter is used, but addition of exogenous inducer is not required. Commonly used constitutive promoters include CMV, EF1a, SV40, PGK1, Ubc, human beta actin, CAG, Ac5, Polyhedrin, TEF1, GDS, ADHI (repressed by ethanol), CaMV35S, Ubi, H1, U6, T7 (requires T7 RNA polymerase), and SP6 (requires SP6 RNA polymerase). Common inducible promoters include TRE (inducible by Tetracycline or its derivatives; repressible by TetR repressor), GAL1 & GAL10 (inducible with galactose; repressible with glucose), lac (constitutive in the absence of lac repressor (LacI); can be induced by IPTG or lactose), T7lac (hybrid of T7 and lac; requires T7 RNA polymerase which is also controlled by lac operator; can be induced by IPTG or lactose), araBAD (inducible by arabinose which binds repressor AraC to switch it to activate transcription; repressed catabolite repression in the presence of glucose via the CAP binding site or by competitive binding of the anti-inducer fucose), trp (repressible by tryptophan upon binding with TrpR repressor), tac (hybrid of lac and trp; regulated like the lac promoter; e.g., tacI and tacII), and pL (temperature regulated). The promoter can be prokaryotic or eukaryotic promoter, depending on the host. Common promoters and their sequences are well known in the art.

As used herein, a "library" refers to a collection or plurality of components to be tested or screened for a desired function. The size of the library can vary depending on the nature of its components. In some embodiments, the library can contain at least 2, at least 5, or at least 10 genetic candidates, preferably from about 5 to about 1,000,000, or from about 10 to about 100,000, or from about 100 to about 10,000 genetic candidates. In some embodiments, the size of the library can correspond to the number of genes of the entire genome (or a subset) of an organism of interest.

As used herein, a "genetic candidate" refers to a genetic element to be tested or screened. In some embodiments, a genetic candidate can be a gene, such as a gene engineered to be under the control of a heterologous promoter. In some embodiments, a genetic candidate can be a plurality of genes that collectively produce a series of interactions among molecules in a cell that leads to a certain product or a change in a cell (e.g., a genetic pathway).

As used herein, "genome" refers to the complete set of genes or genetic material present in a cell or organism, or a subset thereof in certain embodiments.

As used herein, a "homolog" of a gene or protein, "homology," or "homologous" refers to its functional equivalent in another species. The terms "substantial identity" in the context of a peptide indicates that a peptide comprises a sequence with at least 70% sequence identity to a reference sequence, for example at least 80%, at least 85%, at least 90%, at least 95%, at least 96%, at least 97%, at least 98%, or at least 99% sequence identity to the reference sequence, over a specified comparison window. Optionally, optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

As used herein, a "variant" of a gene or nucleic acid sequence is a sequence having at least 10% identity with the referenced gene or nucleic acid sequence, and can include one or more base deletions, additions, or substitutions with respect to the referenced sequence. The differences in the sequences may by the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" of the original sequence. A "variant" of a peptide or protein is a peptide or protein sequence that varies at one or more amino acid positions with respect to the reference peptide or protein. A variant can be a naturally-occurring variant or can be the result of spontaneous, induced, or genetically engineered mutation(s) to the nucleic acid molecule encoding the variant peptide or protein. A variant peptide can also be a chemically synthesized variant.

As used herein, "cofactors" are compounds involved in biochemical reactions that are recycled within the cells and remain at approximately steady state levels. Common examples of cofactors involved in anaerobic fermentation include, but are not limited to, $NAD^+$ and $NADP^+$ and ADP. In metabolism, a cofactor can act in oxidation-reduction reactions to accept or donate electrons. When organic compounds are broken down by oxidation in metabolism, their energy can be transferred to $NAD^+$ by its reduction to NADH, to $NADP^+$ by its reduction to NADPH, or to another cofactor, $FAD^+$, by its reduction to FAD¾. The reduced cofactors can then be used as a substrate for a reductase.

As used herein, "insecticide" refers to a substance used to prevent, destroy, repel, mitigate, or kill insects.

As used herein, "organophosphate" refers to an organophosphorous compound that displays anti-cholinesterase activity.

As used herein, "malathion" refers to an organophosphate pesticide that has the chemical name S-(1,2-dicarbethoxyethyl)-O,O-dimethyldithiophosphate or ((dimethoxy-phosphinothioyl)thio) butanedioic acid, diethyl ester (CAS No. 121-75-5). U.S. Pat. Nos. 3,352,664, 3,396,223, and 3,515,782 describe the use of malathion in pesticides. The disclosure of these references is incorporated by reference.

As used herein, "pest" refers to any organism whose existence it can be desirable to control. Pests can include, for example, arthropod species, such as, for example, an insect, an arachnid, or an arachnoid, bugs, flies and parasites. The pest can be a species belonging to an animal order, such as, for example, Acari, Anoplura, Araneae, Blattodea, Coleoptera, Collembola, Diptera, Grylloptera, Heteroptera, Homoptera, Hemiptera: Cimicidae, Hymenoptera, Isopoda, Isoptera, Lepidoptera, Mantodea, Mallophaga, Neuroptera, Odonata, Orthoptera, Psocoptera, Siphonaptera, Symphyla, Thysanura, Thysanoptera, As used herein, "treatment" means any manner in which one or more of the symptoms of a disease or disorder are ameliorated or otherwise beneficially altered. Treatment also encompasses any use of the compositions herein, such as use for treating, repelling and/or eradicating any ectoparasite or pest. Prevent means to reduce the risk of getting a disease or disorder.

As used herein, "repel" when used in the context of "repelling an insect" means to repulse, ward off, drive back or keep away from a treated surface, such that at any given time, there are fewer insects or pests on a treated locus then on an untreated locus under the same conditions. Although an insect or pest can land on or cross over a treated surface, the insect does not stay on the treated surface for a prolonged period of time or does not stay to probe or bite or otherwise damage the surface.

As used herein, the term "insect repellent" refers to a compound or composition conferring on a subject or locus protection from insects or pests when compared to no treatment at all.

As used herein, "protection" refers to a reduction in numbers of insects, and can, e.g., be usefully determined by measuring mean complete protection time ("mean CPT") in tests in which insect behavior toward treated animals, including humans, and treated inanimate surfaces is observed.

'Trait enhancement" means a detectable and desirable difference in a characteristic in a transgenic plant relative to a control plant or a reference. In some cases, the trait enhancement can be measured quantitatively. For example, the trait enhancement can entail at least about 2% difference in an observed trait, at least about 5% desirable difference, at least about 10% difference, at least about 20% difference, at least about 30% difference, at least about 40%, at least about 50% difference, at least about 60%, at least about 70% difference, at least about 80% difference, at least about 90% difference, or at least about a 100% difference, or an even greater difference. In other cases, the trait enhancement is only measured qualitatively. It is known that there can be a natural variation in a trait. Therefore, the trait enhancement observed entails a change of the normal distribution of the trait in the transgenic plant compared with the trait distribution observed in a control plant or a reference, which is evaluated by statistical methods provided herein. Trait enhancement includes, but is not limited to, yield increase, including increased yield under non-stress conditions and increased yield under environmental stress conditions. Stress conditions can include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability, high plant density, or any combinations thereof.

"Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

As used herein, "including," "comprising," "having," "containing," "involving," and variations thereof, are meant to encompass the items listed thereafter and equivalents thereof as well as additional items. "Consisting of" shall be understood as a close-ended relating to a limited range of elements or features. "Consisting essentially of" limits the scope to the specified elements or steps but does not exclude those that do not materially affect the basic and novel characteristics of the claimed invention.

Other terms used in the fields of recombinant nucleic acid technology and molecular and cell biology and agricultural sciences as used herein will be generally understood by one of ordinary skill in the applicable arts.

Library for Screening

In various embodiments, a library of genetic candidates can be screened using methods and compositions disclosed herein. In some embodiments, the library to be screened can be a library of genes isolated from an organism of interest via, e.g., next-generation sequencing. This organism in question may have a phenotypic feature (e.g., for *Bacillus thuringiensis*, an observation that the bacteria can kill select insects), for which it is hypothesized that the products of individual genes are causing the phenotype, but screening each gene for its produced product using conventional methods is difficult, costly and time consuming. In this case, the library of genes, comprised of all the coding sequences sequenced in the candidate organism, can be individually expressed in individual cell-free systems, and can be individually assayed to identify the gene causing the phenotype.

In some embodiments, the library to be screened can be a library of genes isolated from metagenomic sequences. For example, a specific sequence may be known to have a phenotypic effect, but alternate genes with either a modified (e.g., more potent) phenotypic effect or another desired phenotypic outcome are needed. Metagenomic sequences from a sequence library, such as Pubmed, can be used to identify genes that have substantial similarity or homology (e.g., 95%) to the gene in question. These homologs can then be synthesized, individually expressed, and assayed to identify function using methods and compositions disclosed herein.

In some embodiments, the library to be screened can be a library of genes isolated based on a hypothesis (e.g., genes at the same genomic loci as a gene of known function may have a desired function). Based on this hypothesis, the library can be populated using set algorithms, such as through pulling all genes within a certain genetic distance of the gene of known function. These genes can then be tested using methods and compositions disclosed herein.

In some embodiments, the library to be screened can contain different subunits and/or cofactors that potentiate the activity of a protein. For example, for certain insecticidal toxin classes subunits and/or cofactors may potentiate activity, but may be unknown in identity. The library may be putative subunits and or/cofactors that can then be individually expressed, and combined with the protein to gauge potency.

In some embodiments, the library to be screened can be a library of computational or protein-engineering variants of a gene. The computational or protein-engineering variants can be designed to achieve a certain function (such as resulting protein stability, resulting protein toxicity, etc.). These variants can be de novo synthesized, individually expressed, and assayed to identify function using methods and compositions disclosed herein.

Composition of In Vitro Transcription and Translation

The in vitro transcription and translation system is a system that is able to conduct transcription and translation outside of the context of a cell. In some embodiments, this system is also referred to as "cell-free system", "cell-free transcription and translation", "TX-TL", "TXTL", "TX/TL", "extract systems", "in vitro system", "ITT", or "artificial cells." Exemplary in vitro transcription and translation systems include purified or partially purified protein systems that are made from hosts, purified or partially purified protein systems that are not made from hosts, and protein systems made from a host strain that is formed as an "extract". In an embodiment, extracts include whole-cell extracts, nuclear extracts, cytoplasmic extracts, combinations thereof, and the like. Whole-cell extracts are also termed lysates herein. Lysates, and lysate systems, described herein, are intended to be non-limiting examples of extracts; where lysate is described herein, it is contemplated that other extracts, or extracts and protein combinations, may be used.

In an embodiment, a cell-free system may include a combination of cytoplasmic and/or nuclear components from cells. The components may include extracts, purified components, or combinations thereof. The extracts, purified components, or combinations thereof include reactants for protein synthesis, transcription, translation, DNA replication and/or additional biological reactions occurring in a cellular environment identifiable by a person skilled in the art.

Figure 2:
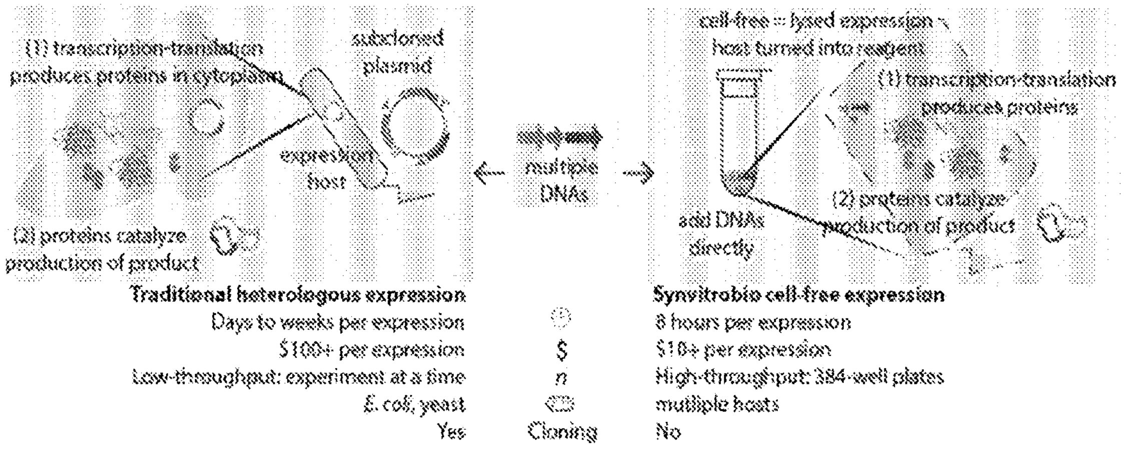
FIG. 2 provides a comparison of traditional heterologous expression to cell-free expression.

Cell-free transcription-translation is described in FIG. 1. Top, cell-free expression that takes in DNA and produces protein that catalyzes reactions. Bottom, diagram of cell-free production and representative data collected in 384-well plate format of GFP expression. Cell-free approaches contrasted to cellular approaches are described in FIG. 2. Cell-free platform allows for protein expression from multiple genes without live cells. Cell-free production biotechnology methods produce lysates from prokaryotic cells that are able to take recombinant DNA as input and conduct coupled transcription and translation to output enzymatically active protein. Cell-free systems take only 8 hours to express, rather than days to weeks in cells, since there is no need for cloning and transformation. They are also at least 10-fold cheaper to run than cells, and can be run in high-throughput as reactions are the equivalent of a reagent and used in a 384-well plate. Typical yields of prokaryotic systems are 750 μg/mL of GFP (30 μM). Cell-free systems can multiple organisms can be implemented and expression conducted at scales from 10 μl up to 10 mL.

Directions on how to make the extract component of cell-free systems, particularly lysates from *E. coli*, can be found in (Sun et al. 2013), which is hereby incorporated by reference herein in its entirety; other methods for producing a lysate are known to one of ordinary skill in the art. While this procedure is adapted for *E. coli* cell-free systems, it can be used to produce other cell-free systems from other organisms and hosts (prokaryotic, eukaryotic, archaea, fungal, etc.) Examples, without limitation, of the production of other cell-free systems include *Streptomyces* spp. (Thompson et al. 1984), *Bacillus* spp. (Kelwick et al. 2016), and Tobacco BY2 (Buntru et al. 2014), which are hereby incorporated by reference herein in their entireties. Exemplary processes for producing lysates involve growing a host in a rich media to mid-log phase, followed by washes, lysis by French Press and/or Bead Beating Homogenization and/or equivalent method, and clarification. A lysate that has been processed as such can be referred to as a "lysate", or a "treated cell lysate", and is a non-limiting example of an "extract". In an embodiment, cells may be grown under anaerobic conditions. In an aspect, an extract may be prepared under anaerobic conditions.

One or more additives may be supplied along-side an extract to maintain gene expression. Contemplated additives include those tailored to replicate the in vivo expression and/or the metabolic environment of the lysate source organism, e.g., redox buffering agents, phosphate potential buffering agents, customized energy regeneration systems, native ribosomes, chaperones, species-specific tRNAs, pH buffering, metals (such as Magnesium and Potassium), osmoregulatory agents, gas concentrations; [O2], [CO2], [N2], sugars, maltose, starch, maltodextrin, glucose, glucose-6-phosphate, fructose-1,6-biphosphate, 3-phosphoglycerate, phosphoenolpyruvate, pyruvate kinase, pyruvate dehydrogenase, pyruvate, acetyl phosphate, acetate kinase, creatine kinase, creatine phosphate, glutamate, amino acids, ATP, GTP, CTP, UTP, ADP, GDP, CDP, UDP, AMP, GMP, CMP, UMP, folinic acid, spermidine, putrescine, betaine, DTT, TCEP, b-mercaptoethanol, TPP, FAD, FADH, NAD, NADH, NADP, NADPH, oxalic acid, CoA, glutamate-salts, acetate-salts, cAMP, native polymerases, synthetic polymerases, phage polymerases, temperature regulation conditions. A review of optional additives can be found in (Chiao et al. 2016), which is hereby incorporated by reference herein in its entirety. Optional additives may also include components that assist transcription and translation, such as phage polymerases, T7 RNA polymerase (RNAP), SP6 phage polymerase, cofactors, elongation factors, nanodiscs, vesicles, and antifoaming agents. Optional additives may also include additives to protect DNA, such as, without limitation, gamS, Ku, junk DNA, DNA mimicry proteins, chi site-DNA, or other DNA protective agents.

In some embodiments, the reaction may include more than 0.1% (w/v) of crowding agent. Macromolecular crowding refers to the effects of adding macromolecules to a solution, as compared to a solution containing no macromolecules. Such macromolecules are termed crowding agents. A contemplated crowding agent may be from a single source, or may be a mix of different sources. The crowding agent may be from varied sizes. In some embodiments, the crowding agents include polyethylene glycol and its derivatives, polyethylene oxide or polyoxyethylene.

An energy recycling and/or regeneration system drives synthesis of mRNA and proteins by providing ATP to a system and by maintaining system homoeostasis by recycling ADP to ATP, by maintaining pH, and generally supporting a system for transcription and translation. A review of energy recycling systems can be found in (Chiao et al. 2016), which is hereby incorporated by reference herein in its entirety. Examples, without limitation, of energy recycling and/or systems that can be used include Glycerate 3-phosphate (3-PGA) (Sun et al. 2013), creatinine phosphate/creatinine kinase (CP/CK) (Kigawa et al. 1999), PANOx (Kim & Swartz 2001), and glutamate (Jewett & Swartz 2004). Other recycling and/or systems include those that can regenerate redox potential ([NAD (P) H]/[NAD (P+)]). An example of redox recycling is described in (Opgenorth et al. 2014). Recycling and/or systems can utilize innate central metabolism pathways from the host (for example, glycolysis, oxidative phosphorylation), externally supplied metabolic pathways, or both.

The in vitro transcription and translation system includes one or more nucleic acids. In an embodiment, the nucleic acid may include DNA, RNA, or combinations thereof. In some embodiments, a DNA may be supplied that that can produce a protein by utilizing transcription and translation machinery in the extract and/or additions to the extract. This DNA may have regulatory regions, such as under the OR2-OR1-Pr promoter (Sun et al. 2013), the T7 promoter or T7-lacO promoter, along with a RBS region, such as the UTR1 from lambda phage. The DNA may be linear or plasmid. In some embodiments, gene sequences may be engineered for cell-free expression in TXTL systems derived from the lysate source organism, such as: 5' rare codons for improved TXTL coupling, 5' AT/GC content for improved TXTL coupling, UTR, RBS, termination sequences, 5' fusions for improved TXTL coupling, gene fusions for improved TXTL coupling, fusions for protein stability, sequence deletions to promote solubility of membrane proteins, and protein tags.

In other embodiments, a mRNA may be supplied that utilizes translational components in the lysate and/or additions to the lysate to produce a protein. The mRNA may be from a purified natural source, or from a synthetically generated source, or can be generated in vitro, e.g., from an in-vitro transcription kit such as HiScribe™, MAXIscript™, MEGAscript™, mMESSAGE MACHINE™, MEGAshortscript™.

In some embodiments, non-canonical amino acids may be utilized in the composition. Non-canonical amino acids may be found naturally in the cellular-produced product, or may be artificially added to the product to produce desirable properties, such as tagging, visualization, resistance to degradation, or targeting. While implementation of non-canonical amino acids is difficult in cells, in cell-free systems implementation rates are higher due to the ability to saturate with the non-canonical amino acid. Examples, without limitation, of non-canonical amino acids, including ornithine, norleucine, homoarginine, tryptophan analogs, biphenylalanine, hydrolysine, pyrrolysine, or as described in (Blaskovich 2016) which is hereby incorporated by reference herein in its entirety.

Production of Products for Direct Testing in a Cell-Free System

An embodiment relates to a method, including providing a composition, wherein a protein is expressed; exposing the composition to assay components; and determining whether the protein reacts to the assay components. In an embodiment, the expression of the protein and the reaction with the assay components occur concurrently. In an aspect, the composition and the assay components are located in the same vessel.

The composition may include an extract derived from one or more organisms; and one or more nucleic acids encoding one or more proteins of interest. In an embodiment, the extract may include a set of cofactors and/or enzymes and/or other reagents necessary for transcription and/or translation. In a further embodiment, the set of cofactors and/or enzymes and/or other reagents necessary for transcription and/or translation may be added to the composition separate from the extract.

In an embodiment, the assay components may include one or more organisms. In an aspect, the organism may include an insect. In an aspect, the reaction of the protein with the organism may result in death of the organism.

An embodiment relates to a method, including providing a composition, wherein a protein is expressed and wherein a product of the protein is made; exposing the composition to assay components; and determining whether the product of the protein reacts to the assay components.

An embodiment relates to a method, including providing a composition, wherein a protein is expressed and wherein a product of the protein is made; exposing the composition to assay components; and determining whether a reaction occurs with the assay components.

In some embodiments, there is an in vitro preparation of a product, comprising providing a composition of an extract derived from one or more organisms; one or more nucleic acids encoding one or more proteins of interest; a set of cofactors and/or enzymes and/or other reagents necessary for transcription and/or translation; and directly utilizing the composition to identify a response with another product.

In some embodiments, the method of preparing the product is used to discover or characterize insecticides. Insecticides can be single or multiple protein products, including but not limited to: Bt, cry, mcf, *Photorhabdus* genes, Xenorhabdus genes, Tc complexes, RiPPs, NRPSs, natural products, and derivatives of natural products. By expressing putative nucleic acids encoding the insecticide in the cell-free system, the insecticide can be made in quantities high enough to directly test for insecticidal activity on a sensitive insect. Toxic or adverse affects can be determined by testing with a negative control (e.g., cell-free system without insecticide expressed). While the cell-free composition, after expression but without concentration, may elicit a response against a target, cell-free composition can also be further concentrated to produce a larger response. Insecticides can also be small molecules that are produced as a result of the cell-free composition.

In some embodiments, the method of preparing the product is used to discover or characterize herbicides. Herbicides can be small molecule compositions that are formed from a reaction of proteins expressed from the nucleic acids, or can be proteins that are expressed directly from the nucleic acids provided to the cell-free composition.

In some embodiments, the method of preparing the product is used to discover or characterize antibiotics. Antibiotics can be small molecules formed from the reaction of proteins expressed from the nucleic acids, or proteins either directly produced in the cell-free composition or formed from the reaction of other proteins expressed from the nucleic acids, and can either kill microbes that are harmful for an agricultural product or can rebalance a microbial population in a manner beneficial to an agricultural product.

In some embodiments, the method of preparing the product is used to discover or characterize seed traits. Identified traits from directly applying the cell-free composition to a product can be programmed heterologously or in recombinant form into a plant to confer the trait to the plant.

In some embodiments, the method of preparing the product is used to discover or characterize crop enhancement components or protective components or microbes. Identified traits can improve the growth of a plant product by providing an effective effect or modifying a microbiome or rhizosphere microbiome in a manner beneficial for plant growth.

In some embodiments, the response of the product is at the molecular or cellular level. This can be if the product where the cell-free composition is applied is a protein of interest, or is a beneficial or harmful microbe of interest, or is a cell line. By observing the response of the protein or the microbe using visual, analytical, or other techniques, the activity of the cell-free composition can be discovered.

In some embodiments, the response of the product is phenotypic. This can be if the product where the cell-free composition is applied is multi-cellular, such as a plant or insect. By observing the phenotypic response using visual, analytical, or other techniques, the activity of the cell-free composition can be discovered. In some embodiments, this is directly observed through the growth (or lack thereof) of insects that consume the cell-free composition. In other embodiments, this is directly observed through the growth (or lack thereof) of insects that are injected with the cell-free composition. Particular phenotypic responses, such as a floppy phenotype from cell-death, can shed further light on the product.

In some embodiments, the response is of organism death. The utilization of the cell-free composition is to identify a toxic component to the organism. The cell-free composition can also be used to understand the titration of the toxic component to understand parameters such as lethal dose (LD), LD50, infective dose (ID), or ID50. Organism death may occur rapidly after presentation with the cell-free composition, or can occur after multiple days after presentation, or can occur after multiple weeks.

In some embodiments, the response is of organism growth. The utilization of the cell-free composition is to identify a beneficial component to the organism. This composition may be directly causing the organism to benefit, or may indirectly cause the organism to benefit. Examples of direct effects, without limitation, include growth hormones and pheromones. Examples of indirect effects, without limitation, include antitoxins, molecules that modify the microbiome or rhizome of the organism, or molecules that encourage photosynthesis of nitrogen fixation. Organism growth may occur rapidly after presentation with the cell-free composition, or can occur after multiple days after presentation, or can occur after multiple weeks.

In some embodiments, the product is further isolated from the cell-free composition. This can occur after testing for further examination of the product, or to obtain greater sensitivity for further testing of the product. Isolation can occur from analytical or physical methods, including but not limited to protein purification, LC-MS, HP-LC, SEC, or forms of chromatography.

In some embodiments, the composition is provided to an organism for testing through a feeding assay. This can be done to identify insecticides or other traits that have oral activity. The trait can be directly fed to the insect, provided in water, or layered over food, among other methods.

In some embodiments, the composition is provided to an organism for testing through a injection assay. This can be done to identify insecticides or other traits that have systemic activity, The injection can happen at different stages of the insect's growth to show different effects dependent on time.

In some embodiments, the nucleic acid supplied to the cell-free composition is in linear DNA format. Linear DNA format allows for a rapid iteration cycle from going from trait sequence to testing, as cloning into plasmid form is avoided. This allows cycle times of 4-8 hours before testing, as opposed to days due to the need to subclone, and provides further advantages for the method for identifying agricultural traits.

Production of Products for Comparisons in a Cell-Free System

In some embodiments, a method is developed for identifying optimal conditions, comprising: providing a composition of an extract derived from one or more organisms, a set of cofactors and/or enzymes and/or other reagents necessary for transcription and/or translation, further conducting multiple compositions, wherein each composition contains one or more nucleic acids encoding one or more proteins of interest, and comparing the product of the multiple compositions to identify the ideal composition.

In some embodiments, the ideal composition is determined by production amount. This can be determined directly or indirectly from observation of a final product.

In some embodiments, the ideal composition is determined by protein produced. The nucleic acid template provided may share similar features, such that the differences between the template are being probed for beneficial or harmful effects. Protein produced can be observed directly from the cell-free composition, such as through conducting the cell-free reaction with FloroTect or other unnaturally labeled fluorescent or colorimetric amino acids and/or charged tRNAs, through tracking against a tag (e.g., His, FIASH, Strep, etc), through SDS-PAGE colorimetric stains (e.g., Coomassie, Silver stain, etc.), or through other analytical techniques. Protein produced can be observed from further processing of the cell-free composition, such as through protein purification.

In some embodiments, the ideal composition is determined by mRNA produced. mRNA produced can be observed directly from the cell-free composition, such as through conducting the cell-free composition with aptamers (Malachite-green, Spinach, or equivalent) or other methods to judge mRNA levels produced.

In some embodiments, the ideal composition is determined by direct testing of the cell-free composition against another product.

In some embodiments, the ideal composition is determined by different combinations of multiple compositions followed by direct testing for a response against another product. In this embodiment, each cell-free composition produces a product. Each composition can then be combined in different combinatoric methods to then be tested. This is particularly useful to determine potentiation of response, if the sum of two proteins produces a later response than each protein individually. An example of this occurs with toxin complex insecticides. This is also useful to understand what proteins comprise a functional complex and to determine compatibility.

In some embodiments, the method is used to identify potentiation or abolition of an effect. This effect may be a cellular, molecular, or phenotypic effect.

In some embodiments, the method is used for codon optimization. In particular, different known or unknown traits may need to be optimized for production in a final plant host. To do so, different codon-optimized variants of a trait can be expressed in a cell-free system and the production level of the variants can help determine which variant to move to the final host. The cell-free systems used can utilize extracts that are similar to the final host (e.g., plant cell-free, wheat-germ cell-free, primary cell-line cell-free, or similar), or can utilize bacterial extracts.

In some embodiments, the method is used to identify internal translation sites. Internal translation sites can produce non-specific and unwanted protein products that impede the expression of the desired protein in the final host. Understanding the expression of internal translation sites, which is encoded in DNA, can improve effectiveness and dosage of the final trait in the final host. The cell-free systems used can utilize extracts that are similar to the final host (e.g., plant cell-free, wheat-germ cell-free, primary cell-line cell-free, or similar), or can utilize bacterial extracts.

In some embodiments, the method is used to identify optimal transcription and translation regulatory units. By changing transcription and translation regulatory units, including but not limited to promoter, enhancer, UTRs, ribosome binding sites, terminators, inhibitors, and DNA sequences, traits can be rapidly optimized for in planta expression and adoption in seed. The cell-free systems used can utilize extracts that are similar to the final host (e.g., plant cell-free, wheat-germ cell-free, primary cell-line cell-free, or similar), or can utilize bacterial extracts.

In some embodiments, the method is used to discover variants of known insecticides, herbicides, antibiotics, pesticides, crop protection components, seed traits, crop enhancement components, protective components or microbes. These variants can be determined through directed engineering approaches, rational engineering approaches, or metagenomic approaches. Using metagenomic approaches, variants can be identified that are more potentiating than the known trait. In addition, variants can be identified using this method that are different enough from an existing intellectual property protected variant to be excluded or evaded by active intellectual property claims.

In some embodiments, the method is used to discover domain-shuffled variants. The method can be used to make different compositions, each with a domain-shuffled variant of a trait, to identify an ideal domain-shuffled variant.

EXAMPLES

Example 1. Direct Killing of *M. sexta* Pest by Producing Insecticide in Cell-Free System

*Manduca sexta*, also known as tobacco hornworm, is a prominent insect pest that can distrupt tobacco and tomato crops, among other crops. Therefore, rapidly identifying insecticides that can control *Manduca sexta* provides an example of utilizing the method for identifying agricultural traits.

Four nucleic acid coding sequences were expressed by cell-free systems. One, Cry1Ac (SEQ ID: 1) (DNA seq: 2430), should have activity as an insecticide either orally or by injection; Two, Mcf (SEQ ID: 2) (DNA seq: 2431), should have activity as an insecticide only by injection; Three, GFP (SEQ ID: 3), should have no activity as an insecticide; and Four, Tcca (SEQ ID: 4) (DNA seq: 2432), should have activity as an insecticide but at high dosages.

Cell-free reactions were run with saturating (greater than 4 nM linear DNA) concentrations of each gene in front of a strong promoter and strong phage-derived UTR (sigma70-UTR1) using the methods of (Sun et. al 2013), incorporated here in its entirety, and incorporating gamS, with the following modification: Each reaction run at 4×100 μL in a 24-well plate at 29° C. These were then put into −80 C for storage.

*Manduca sexta* eggs were obtained from Carolina Biological Supply, Burlington, NC. These were incubated until hatched into larvae through standard experimental conditions (room temperature, 16 hour light/8 hour darkness for growth).

To test oral feeding of traits: when the cell-free reactions with expressed traits were needed, they were removed from the freezer. 96-well plates were prepared where 200 μL of Hornworm Diet, ready-to-use (Carolina Biological Supply, Burlington, NC) were added to the bottom of each well, and 20 μL of cell-free reactions or commercial insecticide or no expressed control or PBS were added to the top of the well. Seven conditions were established: Cry1Ac, Mcf, GFP, Tcca, TXTL, PBS, and commercial insecticide (Safer Brand 5163 Caterpillar II concentrate). For each condition, fifteen larvae were transferred into wells, and the plates were incubated (room temperature, 16 hour light/8 hour darkness for growth) for nine days.

Figure 3:
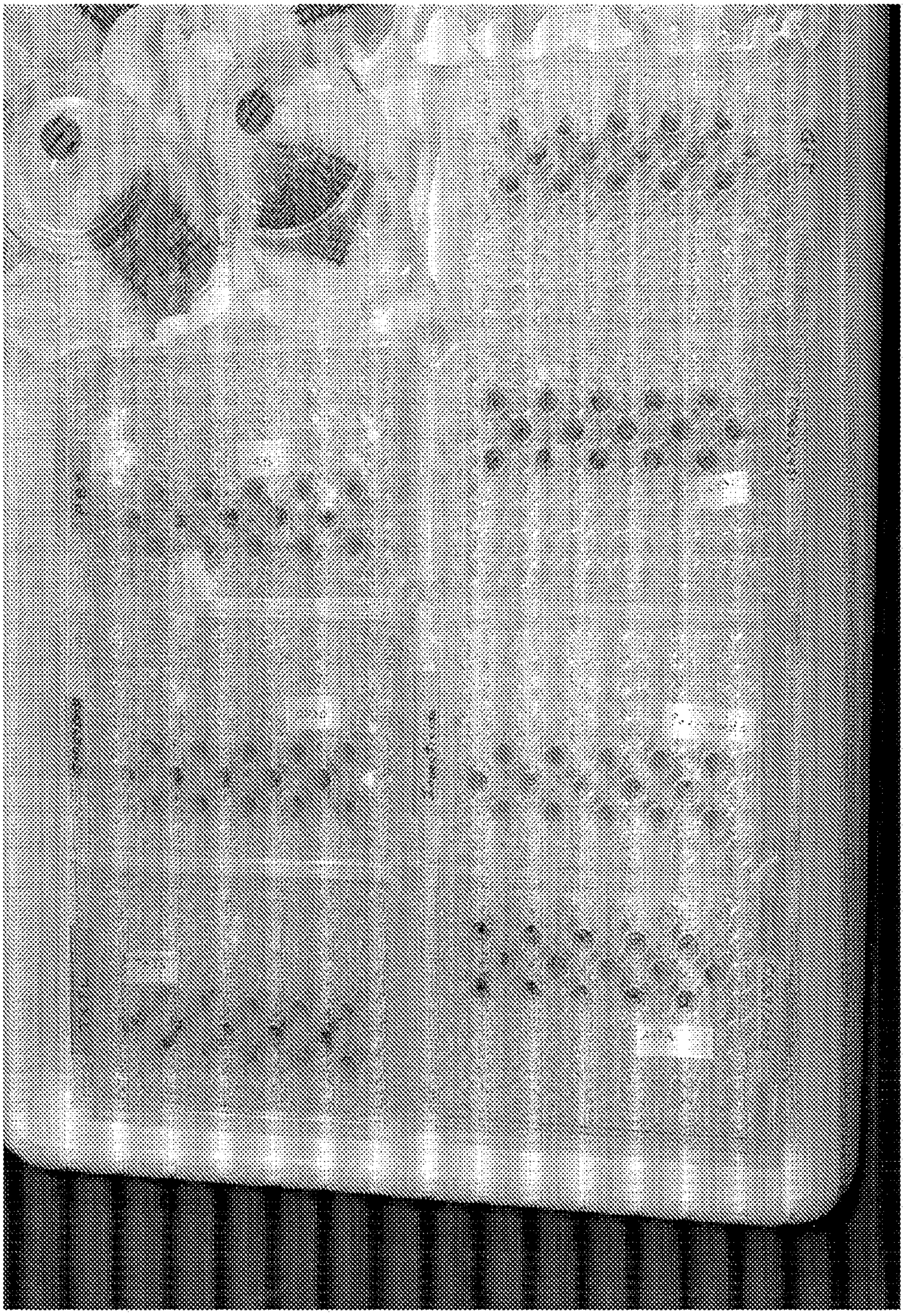
FIG. 3 demonstrates the activity of 20 μL of cell-free expressed traits or of commercially available insecticide over 200 μL growth media used to rear *Manduca sexta*. Shown are seven traits (starting from top left, clockwise: PBS, GFP, Mcf (2431), commercial insecticide *B. thuringensis* var Kurstaki 98%, TccA (2432), TXTL (no expressed DNA), Cry1Ac (2430)). This is taken nine days after introduction of food to *M. sexta* larvae.
Figure 4:
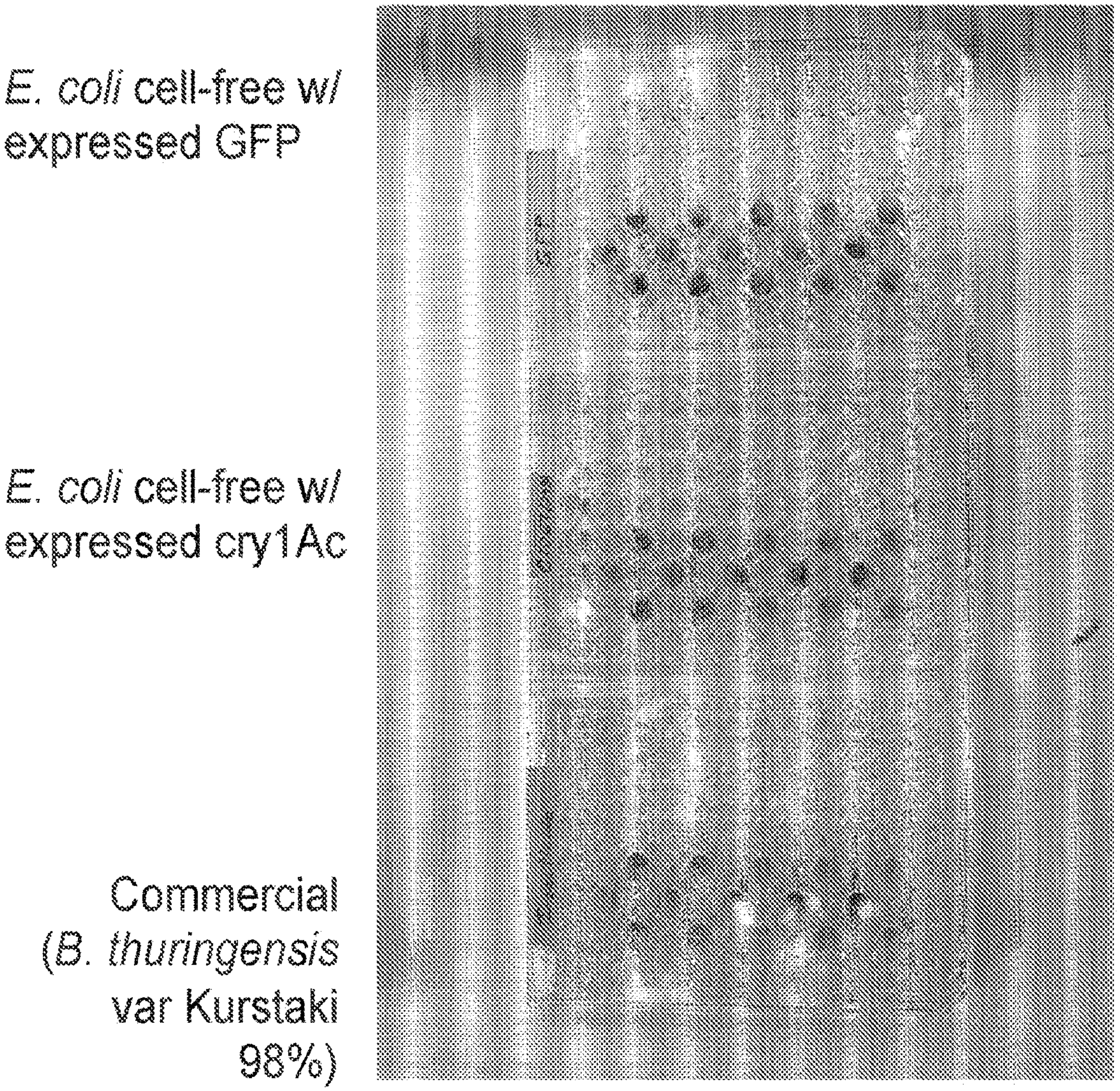
FIG. 4 shows a subset of FIG. 3 for GFP, Cry1Ac, and commercial insecticide *B. thuringensis* var Kurstaki 98%.

After nine days, plates were imaged for viability (FIG. 3; FIG. 4). PBS 8/15, Cry1Ac 15/15, TXTL 7/15, GFP 4/15, Mcf 1/15, Commercial insecticide 15/15, Tcca 5/15 were dead hornworms. This shows that cell-free expressed Cry1Ac, and commercial insecticide had toxic effects against hornworms with direct oral feeding, while other traits or negative controls did not have fully toxic effects against hornworms. Additional negative controls and larger sample sizes can control for smaller effects or for background mortality of hornworms from larvae manipulation.

To test injection of traits: when the cell-free reactions with expressed traits were needed, they were removed from the freezer. Hornworms were reared to the fourth instar larvae stage. They were then injected in batches of seven insects using a Hamilton 30 gauge syringe, (Hamilton, Part 80208), behind the abdominal legs with a 5 μL mixture of 2.5 μL cell-free expressed trait and 2.5 μL water. For each injection, the 30 gauge syringe was rinsed with 70% ethanol followed by water. Hornworms were kept on ice before injection, and later monitored for signs of gut puncture (yellow exudate); if gut puncture occurred, the sample was discarded.

Figure 5:
FIG. 5 shows *Manduca sexta* 1-day post injection with Cry1Ac, Mcf, or GFP, using 50% dilution of 5 μL of cell-free expressed traits. 21 *M. sexta* are present total, with each trait containing 7 injections.
Figure 6:
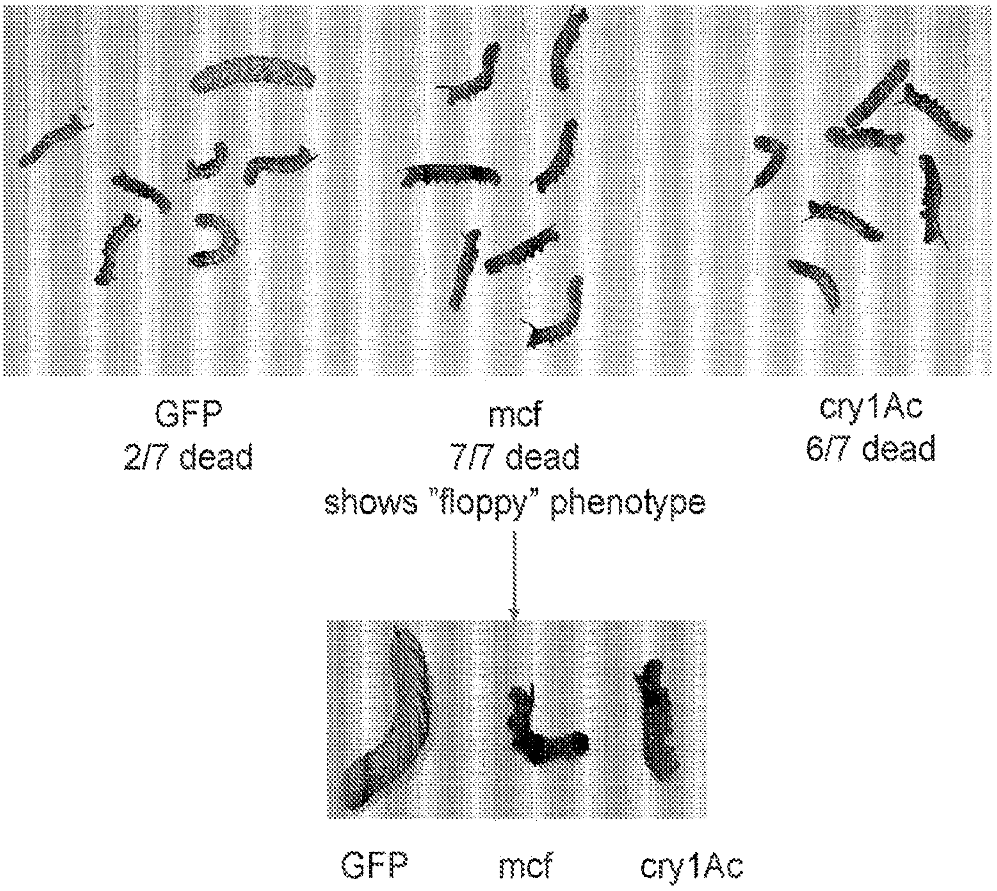
FIG. 6 shows *Manduca sexta* 7-day post injection with Cry1Ac, Mcf, or GFP, using 50% dilution of 5 μL of cell-free expressed traits. 21 *M. sexta* are present total, with each trait containing 7 injections. Also shown is a measure of viability for each trait, and a "floppy" phenotype for Mcf trait.

Three traits were tested: GFP, Mcf, and Cry1Ac. For each trait, injected hornworms were reared in 3 separate cups with access to hornworm diet (FIG. 5) and incubated (room temperature, 16 hour light/8 hour darkness for growth) for seven days (FIG. 6). After day seven, injected hornworms where then analyzed for viability. GFP 2/7, Mcf 7/7, and Cry1Ac 6/7 were dead hornworms, indicating toxicity from Mcf and Cry1Ac injection. In addition, Mcf injected hornworms demonstrated a "floppy" phenotype which has been reported in the literature, demonstrating lack of structure, as compared to the GFP and the Cry1Ac injection. This indicates that direct injection of the trait allows for screening of phenotype and insecticide activity.

While the same cell-free samples were used for oral feeding assays and for injection assays, Mcf showed no activity in oral feeding assays but toxicity in injection assays, while Cry1Ac showed toxicity in both. This is similar to expected phenotypic results reported in the literature.

Those skilled in the art will recognize that the titrations of the injections can be varied to determine the active concentration needed to produce the desired phenotypic response, which allows for understanding of properties such as LD50/IC50. In addition, cell-free produced amounts can be correlated to amounts of protein recovered upon purification to obtain an absolute unit amount of insecticide trait produced.

Figure 7:
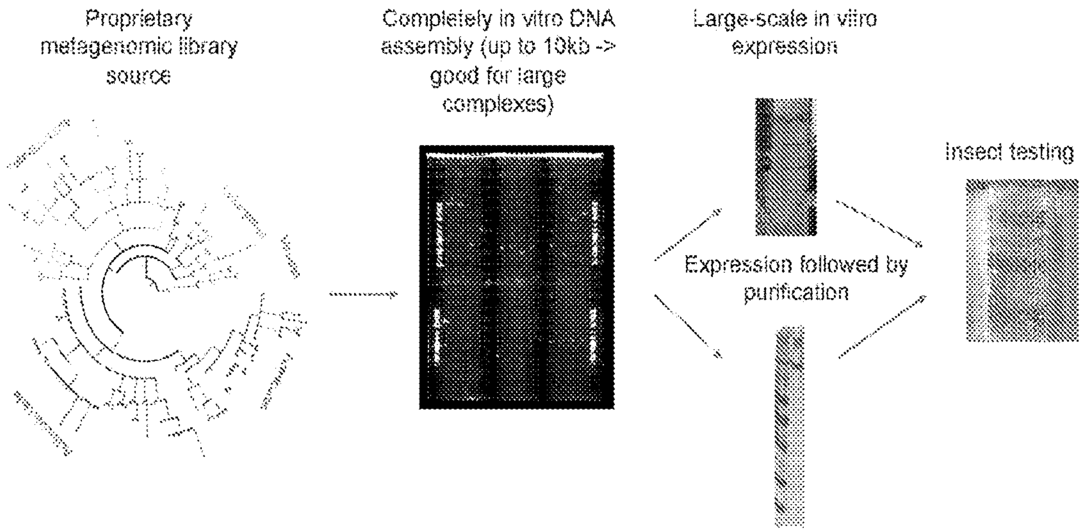
FIG. 7 outlines a method of discovery of traits from metagenomic source, where traits can be determined, genetically synthesized, and then assembled as linear DNA completely in vitro; expressed in vitro in cell-free systems and directly tested for activity; or expressed and then purified for testing for activity.

In one exemplary workflow shown in FIG. 7, genes can be sourced from a metagenomic library; genetically synthesized or otherwise isolated; assembled in vitro into linear DNA; and then either expressed in cell-free systems for direct testing against insects, and/or expressed, purified, and then tested as purified protein against insects.

EQUIVALENTS

The present disclosure provides among other things compositions and methods disclosed herein relate to developing agricultural traits in vitro transcription/translation (TXTL) systems. While specific embodiments of the subject disclosure have been discussed, the above specification is illustrative and not restrictive. Many variations of this disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications, patents and sequence database entries mentioned herein are hereby incorporated by reference in their entirety as if each individual publication or patent or sequence database entry is specifically and individually indicated to be incorporated by reference.

REFERENCES

Blaskovich, M. A. T., 2016. Unusual Amino Acids in Medicinal Chemistry. *Journal of medicinal chemistry,* 59 (24), pp. 10807-10836.

Buntru, M. et al., 2014. Tobacco BY-2 cell-free lysate: an alternative and highly-productive plant-based in vitro translation system. *BMC biotechnology,* 14 (1), p. 37.

Chiao, A. C., Murray, R. M. & Sun, Z. Z., 2016. Development of prokaryotic cell-free systems for synthetic biology. *bioRxiv*, p. 048710.

Jewett, M. C. & Swartz, J. R., 2004. Mimicking the *Escherichia coli* cytoplasmic environment activates long-lived and efficient cell-free protein synthesis. *Biotechnol Bioeng,* 86 (1), pp. 19-26.

Kelwick, R. et al., 2016. Development of a *Bacillus subtilis* cell-free transcription-translation system for prototyping regulatory elements. *Metab Eng,* 38, pp. 370-381.

Kigawa, T. et al., 1999. Cell-free production and stable-isotope labeling of milligram quantities of proteins—Kigawa—1999—FEBS Letters-Wiley Online Library. *FEBS.*

Kim, D.-M. & Swartz, J. R., 2001. Regeneration of adenosine triphosphate from glycolytic intermediates for cell-free protein synthesis. *Biotechnol Bioeng,* 74 (4), pp. 309-316.

Niederholtmeyer, H. et al., 2015. Rapid cell-free forward engineering of novel genetic ring oscillators. *eLife.*

Opgenorth, P. H., Korman, T. P. & Bowie, J. U., 2014. A synthetic biochemistry molecular purge valve module that maintains redox balance. *Nature Communications,* 5, p. 998.

Shin, J. & Noireaux, V., 2012. An *E. coli* Cell-Free Expression Toolbox: Application to Synthetic Gene Circuits and Artificial Cells. *ACS Synth Biol,* 1 (1), pp. 29-41.

Sun, Z. Z. et al., 2014. Linear DNA for Rapid Prototyping of Synthetic Biological Circuits in an *Escherichia coli* Based TX-TL Cell-Free System. *ACS Synth Biol,* 3 (6), pp. 387-397.

Sun, Z. Z. et al., 2013. Protocols for Implementing an *Escherichia Coli* Based TX-TL Cell-Free Expression System for Synthetic Biology. *Journal of Visualized Experiments*, e50762 (79), pp. e50762-e50762.

Takahashi, M. K. et al., 2015. Characterizing and prototyping genetic networks with cell-free transcription-translation reactions. *Methods.*

Thompson, J., Rae, S. & Cundliffe, E., 1984. Coupled transcription—translation in extracts of Streptomyces lividans. *Molecular and General Genetics MGG,* 195 (1-2), pp. 39-43.

The invention claimed is:

1. A method for screening genetic candidates by an in vitro transcription/translation (TXTL) system, comprising:
   - (a) providing a library of genetic candidates to be screened, each genetic candidate encoding one or more protein of interest;
   - (b) expressing each genetic candidate in an in vitro transcription/translation (TXTL) system comprising cell lysates and an energy recycling system, thereby producing a plurality of compositions each comprising the one or more protein of interest; and
   - (c) subjecting the plurality of compositions to an assay for assessing a desired phenotype, thereby determining whether the one or more protein of interest exhibits the desired phenotype.

2. The method of claim 1, wherein the library comprises at least 2, at least 5, or at least 10 genetic candidates.

3. The method of claim 1, wherein the library comprises a genome of an organism of interest.

4. The method of claim 1, wherein the library comprises a plurality of homologs.

5. The method of claim 1, wherein the library comprises a plurality of variants.

6. The method of claim 1, wherein each genetic candidate is a gene or a genetic pathway comprising a plurality of genes.

7. The method of claim 6, wherein each gene is engineered to be under the control of the same promoter.

8. The method of claim 1, wherein each genetic candidate comprises a linear DNA.

9. The method of claim 1, wherein step (b) comprises substantially simultaneously expressing all genetic candidates.

10. The method of claim 1, wherein step (c) comprises substantially simultaneously subjecting the plurality of compositions to the assay.

11. The method of claim 1, wherein the assay comprises an organism, wherein the organism is selected from a group consisting of an insect, a plant, an animal, or a bacterium.

12. The method of claim 11, wherein the desired phenotype comprises death or growth of the organism.

13. The method of claim 11, wherein the subjecting step comprises feeding or injecting each composition to the organism.

14. The method of claim 1, wherein the desired phenotype is selected from a group consisting of insecticide, herbicide, antibiotic, pesticide, crop protection, seed trait, or a combination thereof.

15. The method of claim 1, further comprising comparing the plurality of compositions to one another to identify a final composition having a desired characteristic.

16. The method of claim 15, wherein the desired characteristic production amount, protein produced, mRNA produced, and/or a desired response against another product.

17. The method of claim 1, wherein the genetic candidates are variants having alternate codons encoding the same protein, and wherein the library is used for codon optimization and/or identification of internal translation sites.

18. The method of claim 1, wherein the genetic candidates are variants encoding the same protein, and wherein the library is used to discover domain-shuffled variants.

19. The method of claim 1, wherein the genetic candidates are engineered genes having different genetic elements, and wherein the library is used to identify optimal transcription and/or translation regulatory units.

20. The method of claim 1, further comprising purifying the one or more proteins of interest and subjecting the purified proteins to the assay.

* * * * *